(12) United States Patent
Li

(10) Patent No.: US 9,636,090 B2
(45) Date of Patent: May 2, 2017

(54) MULTIFUNCTION ASPIRATION BIOPSY DEVICE AND METHODS OF USE

(76) Inventor: Rongshan Li, Basking Ridge, NJ (US)

( * ) Notice: Subject to any disclaimer, the term of this patent is extended or adjusted under 35 U.S.C. 154(b) by 1012 days.

(21) Appl. No.: 13/440,038

(22) Filed: Apr. 5, 2012

(65) Prior Publication Data

US 2012/0191008 A1    Jul. 26, 2012

Related U.S. Application Data

(63) Continuation-in-part of application No. 11/688,276, filed on Mar. 2, 2007, now Pat. No. 8,152,738.

(60) Provisional application No. 61/629,022, filed on Nov. 12, 2011, provisional application No. 61/516,971, filed on Apr. 11, 2011, provisional application No. 60/852,798, filed on Oct. 19, 2006, provisional application No. 60/846,036, filed on Sep. 20, 2006, (Continued)

(51) Int. Cl.
| | |
|---|---|
| *A61B 10/00* | (2006.01) |
| *C12M 1/00* | (2006.01) |
| *A61B 10/02* | (2006.01) |
| *A61M 5/32* | (2006.01) |
| *A61B 50/36* | (2016.01) |
| *A61M 5/31* | (2006.01) |

(52) U.S. Cl.
CPC ...... *A61B 10/0283* (2013.01); *A61B 10/0096* (2013.01); *A61B 50/362* (2016.02); *A61M 5/3205* (2013.01); *A61M 5/3276* (2013.01); *A61M 2005/3106* (2013.01)

(58) Field of Classification Search
CPC ....... A61B 10/0283; A61M 2005/3117; A61M 2005/3118; A61M 2005/312; A61M 39/20
See application file for complete search history.

(56) References Cited

U.S. PATENT DOCUMENTS

| 2,693,183 A | 11/1954 | Lockhart |
| 4,375,849 A | 3/1983 | Hanifl |
| (Continued) | | |

FOREIGN PATENT DOCUMENTS

| DE | 19647978 A1 | 5/1998 |
| JP | 1086980 | 3/1989 |
| (Continued) | | |

OTHER PUBLICATIONS

International Preliminary Report on Patentability and Written Opinion for International Application No. PCT/US2012/032261 mailed Oct. 15, 2013.

(Continued)

*Primary Examiner* — Sean Dougherty
(74) *Attorney, Agent, or Firm* — Graham Curtin, P.A.

(57) ABSTRACT

One embodiment of a multifunction aspiration biopsy device includes a hub having a chamber for receiving a collected specimen, a vacuum source in communication with the hub chamber, a needle detachable from the hub and having an outlet in communication with the hub chamber, and a cover extending over a portion of the needle outlet for directing a specimen collected through the needle into the hub chamber in a direction that differs from a longitudinal axis of the needle. The hub chamber with collected specimen may be separated from the vacuum source and the needle and the specimen may be triaged within the hub chamber. Various embodiments of a collection container for receiving used needles are also disclosed.

13 Claims, 30 Drawing Sheets

Related U.S. Application Data provisional application No. 60/783,881, filed on Mar. 20, 2006.

(56) References Cited

U.S. PATENT DOCUMENTS

| | | | |
|---|---|---|---|
| 4,799,494 A * | 1/1989 | Wang | 600/566 |
| 4,807,344 A | 2/1989 | Kelson et al. | |
| 4,875,265 A | 10/1989 | Yoshida | |
| 4,989,307 A | 2/1991 | Sharpe et al. | |
| 5,074,312 A | 12/1991 | Sarstedt | |
| 5,137,710 A | 8/1992 | Smalley et al. | |
| 5,188,617 A | 2/1993 | Linder | |
| 5,199,441 A | 4/1993 | Hogle | |
| 5,249,680 A | 10/1993 | Shillington | |
| 5,273,161 A | 12/1993 | Sagstetter | |
| 5,301,685 A | 4/1994 | Guirguis | |
| 5,312,346 A | 5/1994 | Han | |
| 5,330,443 A | 7/1994 | Powles | |
| 5,474,181 A | 12/1995 | Shillington et al. | |
| 5,482,207 A | 1/1996 | Nelson et al. | |
| 5,575,778 A | 11/1996 | Hardt et al. | |
| 5,645,537 A | 7/1997 | Powles et al. | |
| 5,649,911 A | 7/1997 | Trerotola | |
| 5,791,471 A | 8/1998 | Radmand | |
| 5,902,279 A | 5/1999 | Powles et al. | |
| 5,947,950 A | 9/1999 | Shillington et al. | |
| 6,247,592 B1 | 6/2001 | Racicot et al. | |
| 6,465,242 B1 | 10/2002 | Kanipayor et al. | |
| 2002/0049391 A1 | 4/2002 | Kuracina | |
| 2003/0187406 A1 | 10/2003 | Spofforth | |
| 2004/0121456 A1 | 6/2004 | Fischer | |
| 2005/0101879 A1 | 5/2005 | Shidham et al. | |
| 2005/0113715 A1 | 5/2005 | Schwindt et al. | |
| 2007/0218542 A1 | 9/2007 | Li | |

FOREIGN PATENT DOCUMENTS

| | | |
|---|---|---|
| WO | 84/04068 | 10/1984 |
| WO | 2007109639 A2 | 9/2007 |

OTHER PUBLICATIONS

International Search Report and Written Opinion for International Application No. PCT/US2007/064343 mailed Nov. 19, 2008.
Extended European Search Report dated Mar. 5, 2015 in corresponding European Application No. 12771046.5.

* cited by examiner

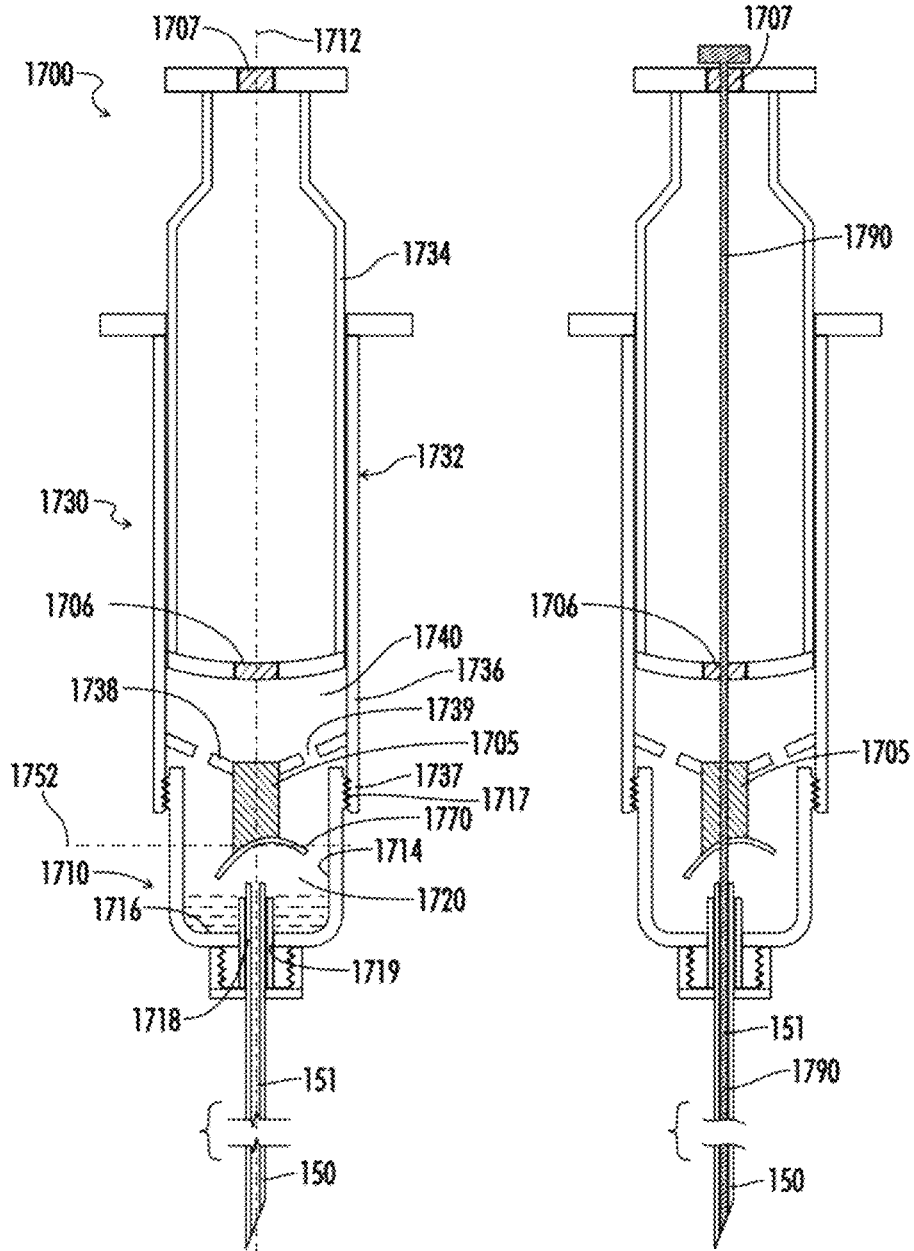
*FIG. 17A*  *FIG. 17B*

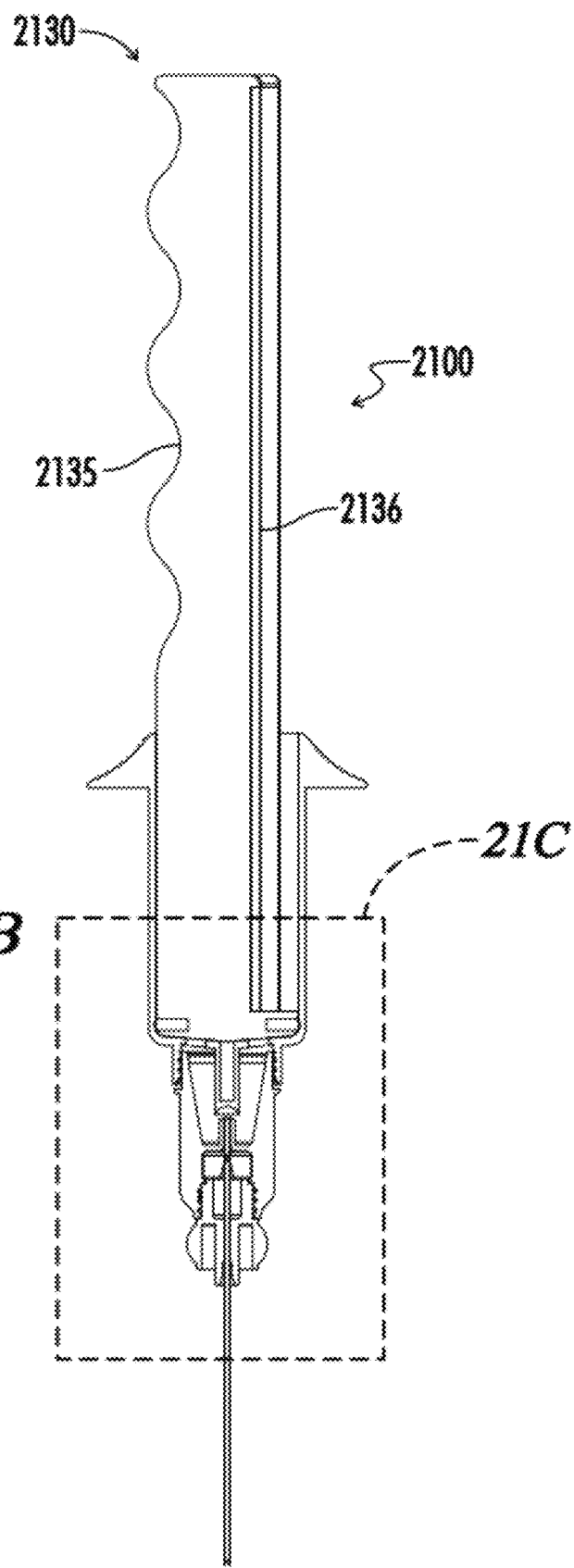

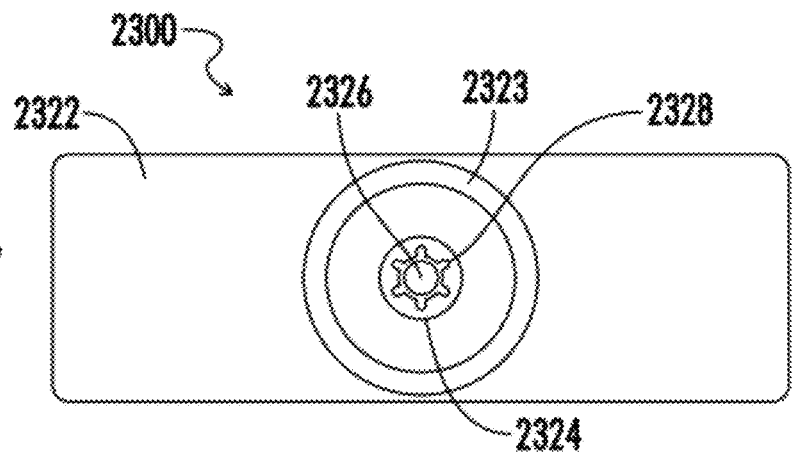
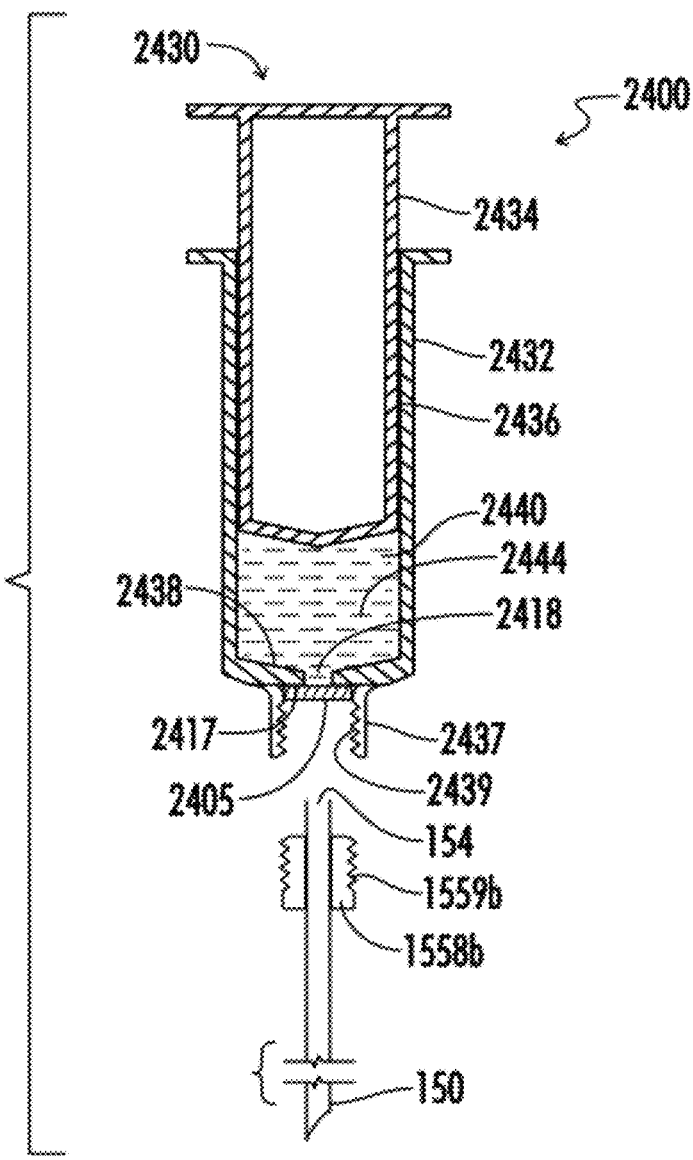

MULTIFUNCTION ASPIRATION BIOPSY DEVICE AND METHODS OF USE

CROSS-REFERENCE TO RELATED APPLICATIONS

This application claims the benefit under 35 U.S.C. §119(e) from U.S. Patent Application 61/516,971, filed Apr. 11, 2011, and from U.S. Patent Application 61/629,022, filed Nov. 12, 2011. This application is also a continuation-in-part of pending U.S. patent application Ser. No. 11/688,276, filed Mar. 20, 2007, which claims the benefit under 35 U.S.C. Section §119(e) from U.S. Patent Application 60/852,798 filed on Oct. 19, 2006, and U.S. Patent Application 60/846,036 filed on Sep. 20, 2006, and U.S. Patent Application 60/801,759, filed on May 20, 2006, and U.S. Patent Application 60/783,881 filed on Mar. 20, 2006. The contents of each of the above applications are incorporated by reference herein.

BACKGROUND

Fine needle aspiration (FNA) is a widely used screening diagnostic procedure. However, only a small and finite amount of material can be obtained by FNA. The current process in the clinical laboratory does not maximally use this limited amount of material. As a result, there is typically only enough material obtained to perform initial or screening tests. The limited amount of material collected through this procedure largely inhibits further classification of the disease, which results in more invasive procedures for a more conclusive diagnosis. This not only results in increased costs, but significantly delays the diagnosis as well.

Personalized medicine and biomarker identification become more and more important in the modern medicine, especially in cancer diagnosis and treatment. Fewer amount of specimen for more tests will be the trend of the future. FNA appears to be the best procedure for this purpose. Current FNA devices have many limitations, including that the device can only be used for cell/tissue collection. Once collected, the specimen has to be transferred to different containers for further transportation to different location for further tests and each additional transfer will cause loss of portion of the specimen and time-consuming. In addition, multiple different tests require multiple individual devices collecting specimen from the same lesion which cause variation from each device and collection. In addition, the sharp needle may cause incidental injury to operators and increase the risks of blood-borne infections such as HIV and hepatitis.

The need remains for a safer systems and methods which maximize the use of this limited material for different tests to permit a more conclusive diagnosis, information collection and time-saving to be made by a single FNA procedure alone and without the need for more invasive procedures.

Current FNA and needle biopsy procedures have certain additional side effects, including hemorrhage, pneumothorax, spreading the tumor cells along the needle pathway, et al. when the needle passes through different tissues to get into the target lesion. It is important to stop and at least reduce the extent of this damage. One method that appears to be helpful is to seal the needle pathway when the needle is drawn out of the body after having finished the cell or tissue collection. In other situations, the physicians need to inject medical materials (such as treatment or diagnostic chemicals) into the target lesion areas first and followed by collecting cells and tissues from the same areas.

There is a need, therefore, for a safer FNA system and method that addresses such side effects. In one embodiment of the present disclosure, there is provided a needle detachable syringe combined with a needle detachable cell/tissue collecting device. In one embodiment, there is provided a syringe with a detachable needle that contains chemicals in the syringe, such that when the needle reaches the target lesion areas the chemicals are injected into the lesion areas. Then the syringe detaches from the needle, the needle remains in its position, a collecting device is then attached to the proximal portion of the needle and start to collect the cells and/or tissues. In another embodiment, the collecting device with detachable needle is used first, where the needle reaches the target lesion areas to collect the cells or tissue, then the needle is detached and remains in position, wherein the needle detachable syringe containing chemicals (which, in one embodiment, seals the needle pathway) is attached to the proximal portion of the needle, and the chemical material is injected into the needle pathway when the needle is drawn from the lesion areas to the outside of the body.

Additional features and benefits will be realized through the various embodiments described herein.

SUMMARY

Various embodiments of a multifunction aspiration biopsy device for fine needle aspiration are disclosed. In one embodiment there is provided a multifunction aspiration biopsy device including a hub having a chamber for receiving a collected specimen, a vacuum source in communication with the hub chamber, a needle detachable from the hub and having an outlet in communication with the hub chamber, and a cover extending over a portion of the needle outlet for directing a specimen collected through the needle into the hub chamber in a direction that differs from a longitudinal axis of the needle. The hub chamber with collected specimen may be separated from the vacuum source and the needle and the specimen may be triaged within the hub chamber. Various embodiments of a collection container for receiving used needles are also disclosed.

BRIEF DESCRIPTION OF THE DRAWINGS

FIG. 17A illustrates an alternative embodiment of an aspiration device with seals and FIG. 17B illustrates an embodiment of the device of FIG. 17A combined with a stylet.

FIG. 19H illustrates a close-up view of one embodiment of a portion of a biopsy device approaching a component of an embodiment of the container shown in FIG. 19G, while

FIG. 21B illustrates a cross-section of the device of FIG. 21A.

FIG. 23C illustrates one embodiment of a diagrammatic top view of a component of the container of FIG. 23A.

FIG. 24 illustrates one embodiment of an injection system used in connection with an embodiment of a multifunction aspiration biopsy device of the invention.

DETAILED DESCRIPTION OF THE PREFERRED EMBODIMENTS

Figure 1A:
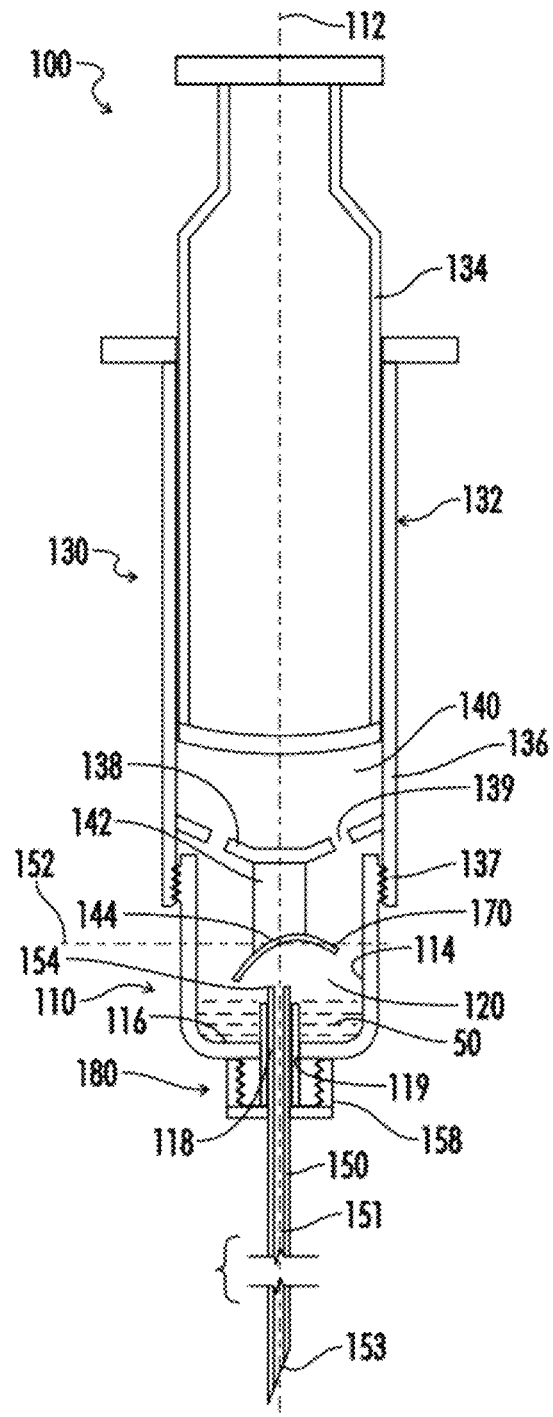
FIG. 1A illustrates one embodiment of an aspiration device.

This disclosure describes the best mode or modes of practicing the invention as presently contemplated. This description is not intended to be understood in a limiting sense, but provides an example of the invention presented solely for illustrative purposes by reference to the accompanying drawings to advise one of ordinary skill in the art of the advantages and construction of the invention. In the various views of the drawings, like reference characters designate like or similar parts.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

FIG. 1A illustrates one embodiment of a multifunction aspiration biopsy device 100 that is typically used for the purpose of, but not limited to, aspirating cells and/or tissues from a target lesion, and having certain components that can function as, for example, a centrifugation tube, a transferring tube, a test tube, a culture tube and a tube for cell block preparation. Other functionalities are possibility within the scope of the present disclosure.

Figure 2:
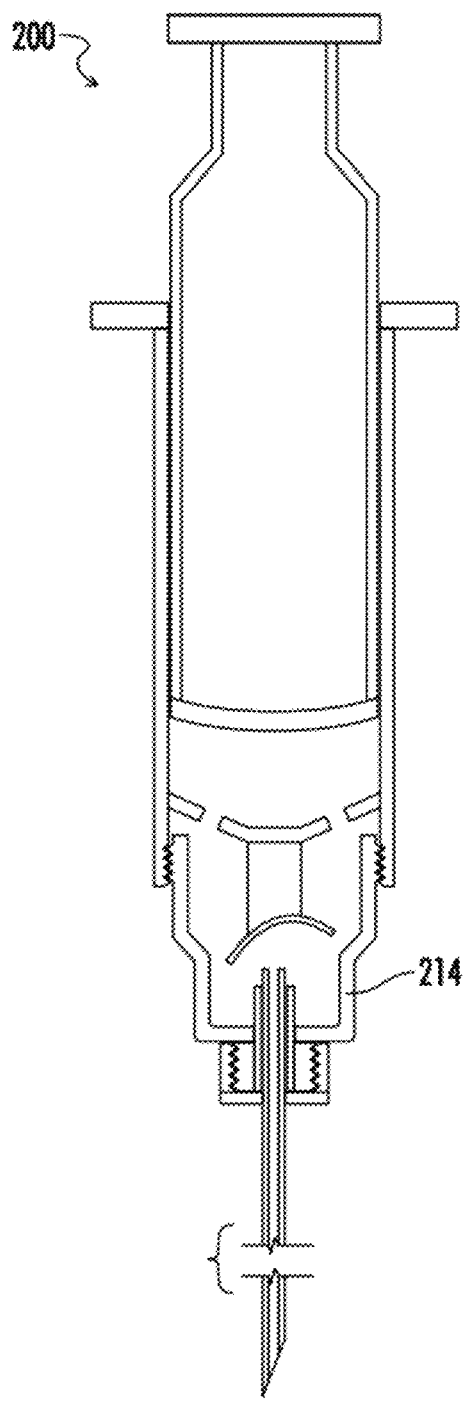
FIG. 2 is an alternative embodiment of an aspiration device.
Figure 3A:
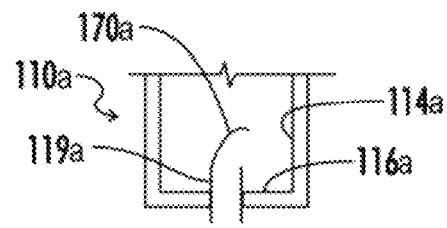
FIGS. 3A through 3D illustrate various embodiments of a cover.
Figure 3B:
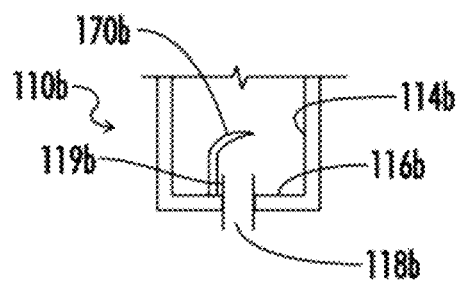
Figure 3C:
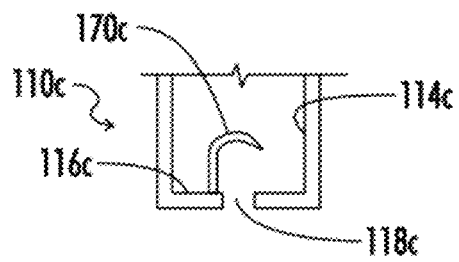
Figure 3D:
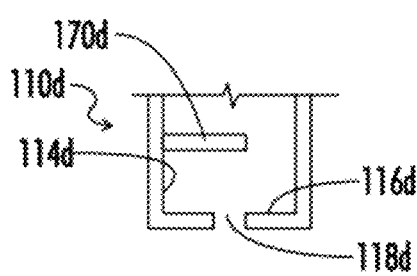

Device 100 of the embodiment of FIG. 1A further comprises a hub 110 having a longitudinal axis 112 and a sidewall 114 extending to a floor 116 to form a chamber 120. The floor 116 has a channel 118 bounded by channel walls 119 that form a passage for the needle 150. While the sidewall 114 is shown in FIG. 1A with a consistent diameter, for example, it will be appreciated that other configurations are possible, such as, but not limited to a tapered sidewall 214 of the device 200 of an alternative embodiment of FIG. 2. Other configurations are possible.

Figure 1B:
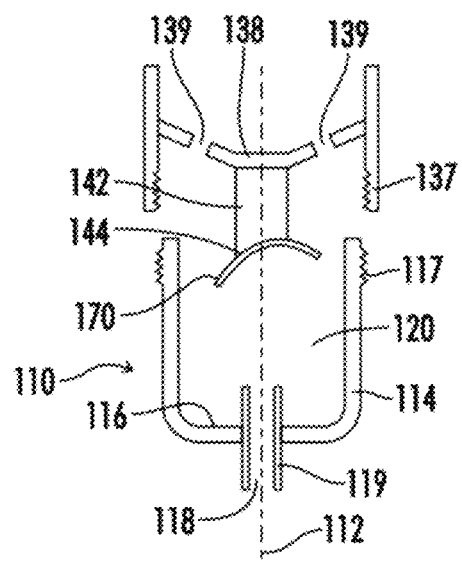
FIG. 1B is one embodiment of a close up view of a portion of the device of FIG. 1A.

Returning to FIG. 1A, device 100 also comprises a vacuum source 130 in communication with the chamber 120, a needle 150 having an inner lumen 151 detachably extending along the longitudinal axis 112 of the hub 110 through the channel walls 119 of the channel 118 in the floor 116 and having a needle inlet 153 and a needle outlet 154 along the longitudinal axis 112 and in communication with the hub chamber 120, and a cover 170 extending over a portion of the needle outlet 154 along a second axis 152 that differs from the longitudinal axis 112 for directing a specimen 50 collected through the needle 150 into the chamber 120 in a direction that differs from the longitudinal axis 112. The vacuum source 130 further comprises a barrel 132 and a plunger 134 movable within the barrel 132. The barrel 132 further comprises a sidewall 136 having an end 137 that engages the hub 110, and a barrel floor 138 that limits movement of the plunger 134 relative to the barrel 132, the barrel floor 138 and barrel sidewall 136 defining a barrel chamber 140. The barrel floor 138 further comprises at least one opening 139, and preferably a plurality of openings 139 for communication between the barrel chamber 140 and the hub chamber 120. FIG. 1B illustrates one manner of engagement between the barrel 132 and the hub 110 where the sidewall end 137 of the barrel 132 is threaded to engage a threaded end 117 of the sidewall 114 of the hub 110. Other methods of engagement are possible.

When the needle inlet 153 is positioned in a target area and specimen 50 to be collected, and when the plunger 134 is withdrawn through the barrel 132, a vacuum is created in both the barrel chamber 140 and the hub chamber 120 through the at least one opening 139 in the barrel floor 138. The specimen 50 from the target area is drawn through the needle inlet 153 to the needle outlet 154 along the longitudinal axis 112 of the hub such that when the specimen 50 reaches the needle outlet 154 it will want to continue traveling along the longitudinal axis 112 of the hub 110 toward the vacuum source 130. The cover 170 redirects the specimen away and along an axis 152 that differs from the longitudinal axis 112 of the hub 110 and toward the sidewall 114 of the hub 110 and onto the hub floor 116 where it collects in preparation for sampling and analysis. Thus, the specimen 50 is retained within the hub chamber 120 and not drawn into the barrel chamber 140 through the one or more openings 139.

Figure 1C:
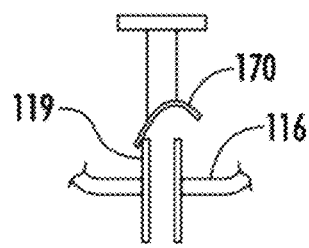
FIG. 1C is a close up view of an alternative embodiment of a portion of the device of FIG. 1A.

In the embodiment of FIG. 1A, the cover 170 is preferably angled to direct a specimen 50 away from the longitudinal axis 112 and toward the hub floor 116. In addition, the cover 170 of the embodiment of FIGS. 1A and 1B is formed at a terminus 144 of a downward extension 142 of the barrel floor 138 and is integral with the barrel floor 138 and is spaced from the needle outlet 154 along the longitudinal axis 112. However, as shown in the embodiment of FIG. 1C, the cover 170 may also be positioned in close proximity to or touching the channel walls 119 such that the cover 170 is also in close proximity to or touching the needle outlet 154 (not shown in FIG. 1C) for directing the specimen toward the hub floor 116.

However, the cover may also be associated with the hub 110 instead of the barrel 132 and may be positioned within the hub 110 as shown, for example, in FIGS. 3A through 3D that illustrate various non-limiting embodiments of a cover 170a-170d positioned on a hub 110a-110d. In the hub embodiment 110a of FIG. 3A, cover 170a forms an integral extension of one of the channel walls 119a such that the channel wall 119a and the cover 170a form a continuous wall for directing a specimen toward the sidewall 114a and the hub floor 116a. In the hub embodiment 110b of FIG. 3B, cover 170b extends from the hub floor 116b and is positioned adjacent one of the channel walls 119b and over the channel 118b for directing a specimen toward the sidewall 114b and the hub floor 116b. In the hub embodiment 110c of FIG. 3C, cover 170c extends from the hub floor 116c and is positioned adjacent and over the channel 118c through which a needle (not shown) will extend for directing a specimen toward the sidewall 114c and the hub floor 116c. In the hub embodiment 110d of FIG. 3D, cover 170d extends from the sidewall 114d and is positioned over the channel 118d through which a needle (not shown) will extend for directing a specimen toward the sidewall 114d and the hub floor 116d. In each of the hub embodiments illustrated herein, the cover extends over the channel to direct the specimen away from the longitudinal axis of the hub and away from the vacuum source (not shown).

Figure 4:
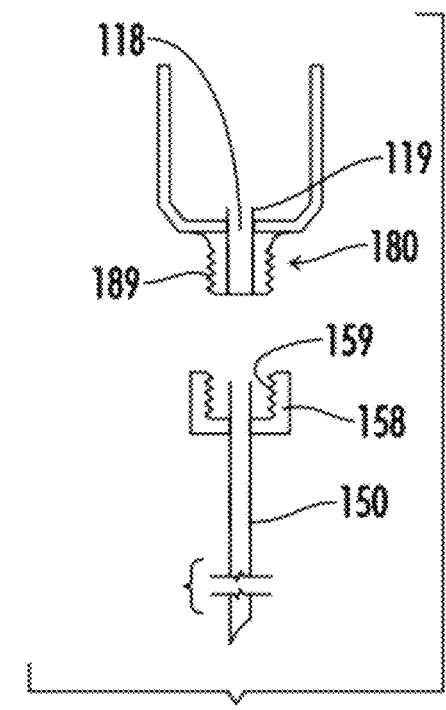
FIG. 4 illustrates one embodiment of a partially exploded view of a needle holder and hub.
Figure 5:
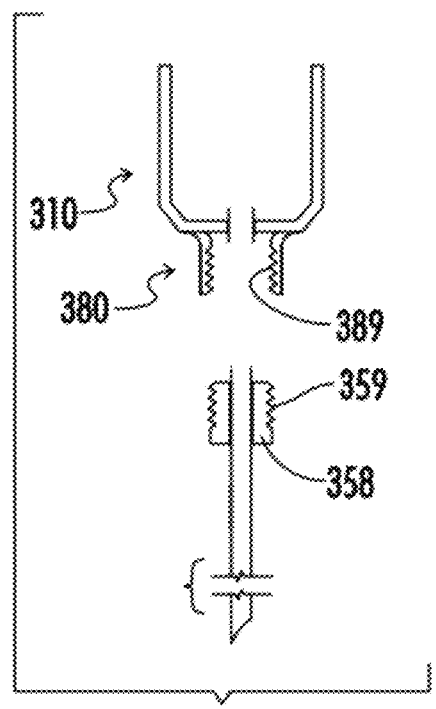
FIG. 5 illustrates one embodiment of a partially exploded view of a needle holder and hub.

Returning to FIG. 1A, the needle 150 is preferably detachably connected to the hub 110 through the engagement of a needle holder 158 with a hub extension 180. More specifically as shown in the embodiment of FIG. 4, needle holder 158 is provided with an inner thread 159 that engages an outer thread 189 on the hub extension 180, wherein the needle 150 extends through the channel walls 119 of the channel 118 during engagement of the needle holder 158 with the hub extension 180. In this embodiment, the diameter of the needle 150 is slightly smaller than the diameter of the channel walls 119. Thus, the needle 150 is capable of being easily inserted through the channel walls 119 and screwed onto and off of the hub extension 180.

Figure 6A:
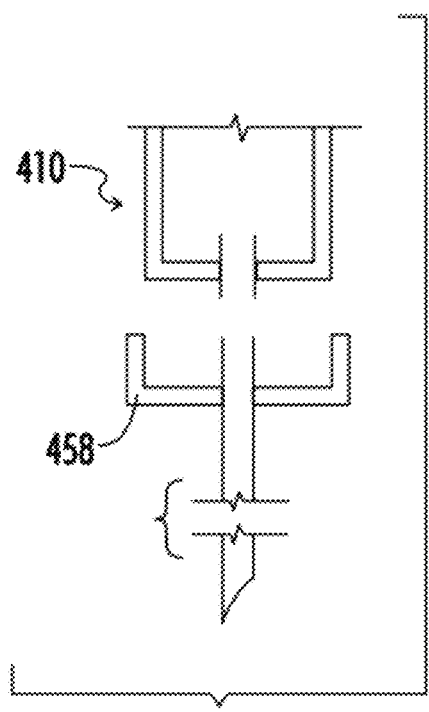
FIG. 6A illustrates one embodiment of a partially exploded view and FIG. 6B illustrates a partially assembled view of a needle holder and hub.
Figure 6B:
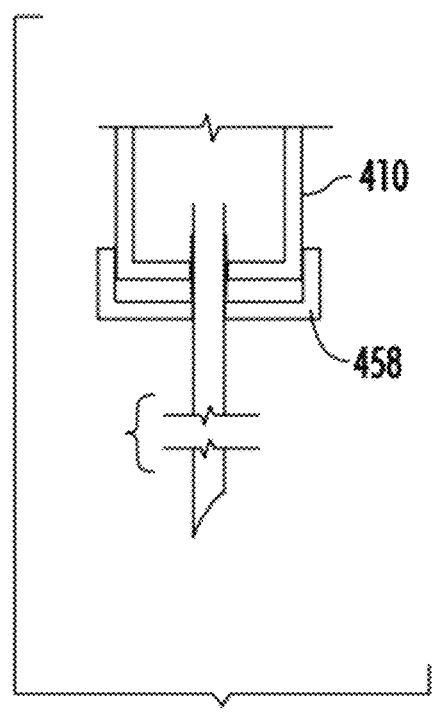

While FIG. 4 illustrates one manner of engagement, alternative engagements are possible. For example, in an alternative embodiment of a hub 310 shown in FIG. 5, a needle holder 358 is provided with an outer thread 359 that engages an inner thread 389 on the hub extension 380. FIGS. 6A and 6B illustrate yet another embodiment of a hub 410 that is not provided with a hub extension, but is instead engaged directly by a needle holder 458 that is press fit into engagement with the hub 410 as shown in FIG. 6B. Whiles FIGS. 4 through 6B show various engagements between the needle and the hub, other engagements are possible. For example, the needle holder may be provided with a quick connect type of connection that mates with a similar quick connect type of connection on the hub. Alternatively, a bayonet type of connection may be employed where the needle holder is pushed onto the hub and then rotated into a locking engagement with the hub. Other methods of engagement are possible, such as a pop-in type of arrangement.

Figure 7A:
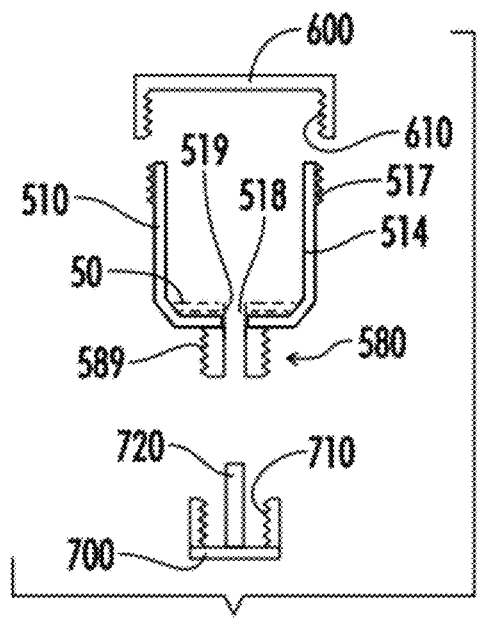
FIG. 7A is an exploded view and FIG. 7B is an assembled view of one embodiment of a hub sealed by a cap and a plug.
Figure 7B:
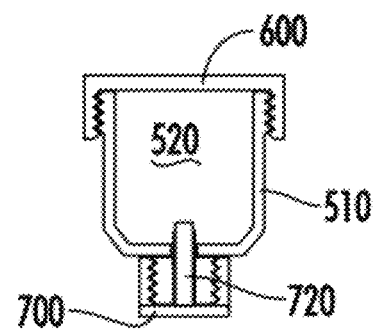

FIG. 7A is an exploded view and FIG. 7B is an assembled view of one embodiment of a hub 510 (including a specimen 50 for purposes of explanation) that has been separated from a vacuum source (not shown) and needle (not shown) and that is transformed into a sealed chamber 520 environment that can function in a non-limiting manner as a centrifuge tube, a specimen transferring tube, a test tube, a culture tube, etc. More specifically, a cap 600 having an inner thread 610 is threadingly engaged with a threaded end 517 of the sidewall 514 of the hub 510. A plug 700 having an inner thread 710 and a core 720 is engaged with the hub extension 580 of the hub 510 such that the inner thread 710 engages the outer thread 589 on the hub extension 580 and the core 720 extends through the channel walls 519 and seals the channel 518. While FIGS. 7A and 7B show certain inner and outer threaded alignments, it will be appreciated that such alignments can be reversed (i.e. the cap can include an outer thread that engages an inner thread on the hub wall), and it will also be appreciated that other manners of engagement are possible. Thus, once a specimen 50 has been collected within the hub chamber, the needle is unscrewed or otherwise detached from the hub and safely disposed of, and the hub is unscrewed or otherwise detached from the vacuum source, and the hub with specimen can then be sealed to retain the specimen in preparation for further analysis and testing.

Figure 8:
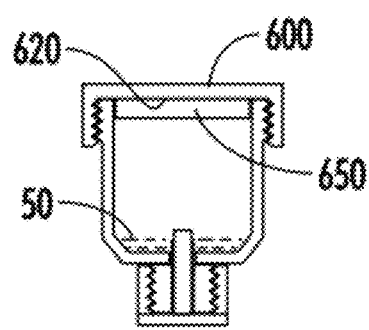
FIG. 8 illustrates one embodiment of a sealed hub assembly including a moisture matrix on a cap.

FIG. 8 illustrates the sealed hub environment of FIGS. 7A and 7B, but with the addition of a moisture matrix 650 attached to the inner surface 620 of the cap 600 to transform the sealed environment into a moisture tube. The moisture matrix 650 may be composed of, but not limited to, a sponge, filter paper or other different material, and it may be wetted by using different fluids according to different user requirements including, but not limited to, saline (such as, for example, 0.9% NaCl), formaldehyde, etc. The wet moisture matrix 650 keeps the collected specimen 50 from drying during transferring from one location to another.

Figure 9:
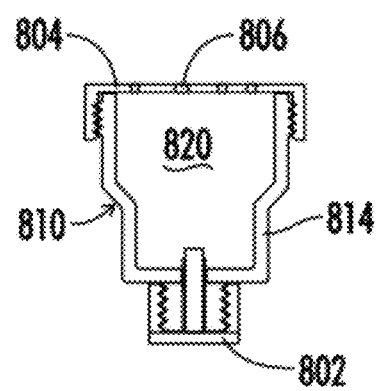
FIG. 9 illustrates one embodiment of a hub assembly including a vented cap.

FIG. 9 illustrates an alternative embodiment of a hub 810 having a tapered sidewall 814, a plug 802 and a cap 804 having one or more holes 806 that function as vents and enable the passage of air into the hub chamber 820 and that enable the hub 810 to function as a culture tube. The holes 806 may be any shape or size and may or may not be covered by a filter (not shown) to keep the hub chamber 820 sterilized.

Figure 10:
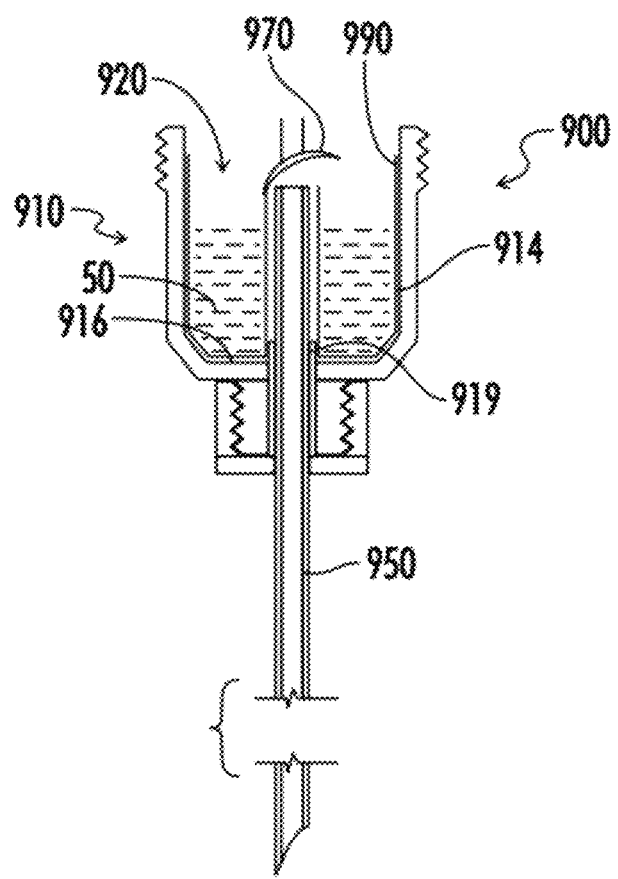
FIG. 10 illustrates one embodiment of an aspiration device having a removable container.

FIG. 10 illustrates an alternative embodiment of a device 900 having a hub 910 with a sidewall 914 and a floor 916 defining a chamber 920, a removable container 990 seated within the chamber 920 along the sidewall 914 and floor 916, a needle 950 extending through the channel walls 919 in the hub floor 916, and a cover 970 for directing the collected specimen 50 into the container 990. The container 990 may be composed of different materials such as, but not limited to, plastic, filter paper, etc. and it may be solid or in a form of a filter bag, web, etc., and may be any shape, size or material composition. The material forming of the container 990 may be soft or hard, and may be porous or solid, or may be in the form of a filter that enables certain fluid, cells or molecules to pass through its walls. The container 990 may receive the collected specimen 50 guided by the cover 970 and may be removable and detachable from the hub chamber 920 and used for different test procedures at different times during an aspiration procedure.

Figure 11:
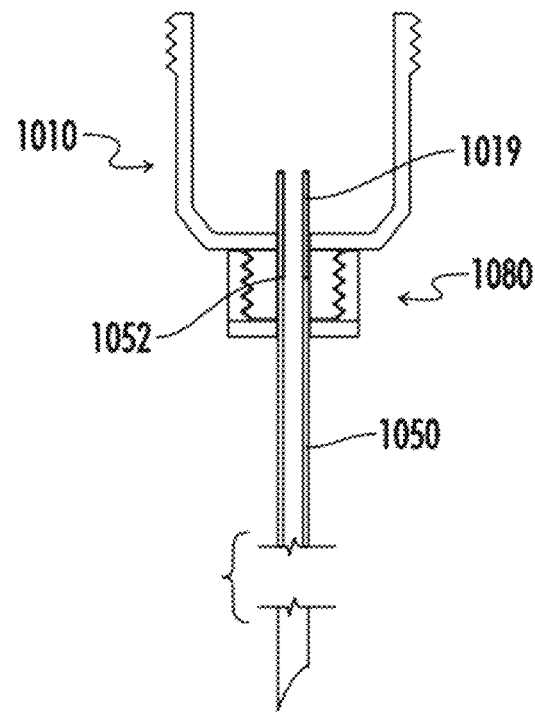
FIG. 11 illustrates one embodiment of a portion of a device having a needle aligned with a hub channel wall to form a continuous lumen.

FIG. 11 illustrates yet another embodiment of a hub 1010 having a channel wall 1019 that is the same diameter as a needle 1050 attached to the hub extension 1080, such that the needle 1050 and channel wall 1019 will sealingly abut at a joint location 1052 and form a single unified lumen.

Figure 12A:
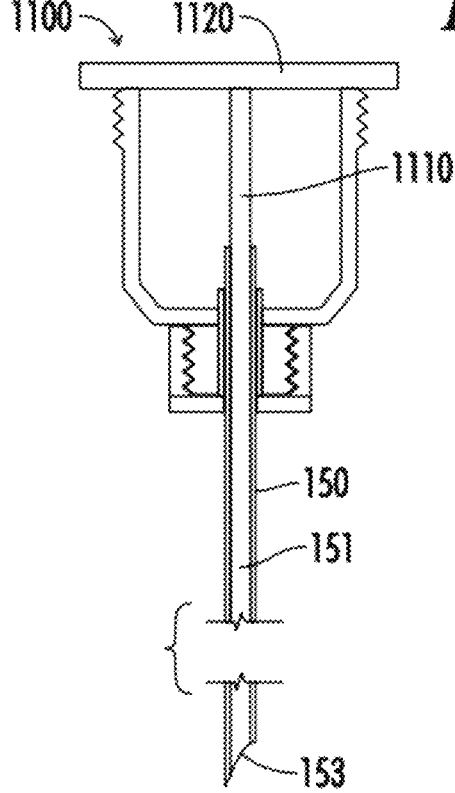
FIGS. 12A and 12B illustrate alternative embodiments of a stylet usable with a device of the present disclosure.
Figure 12B:
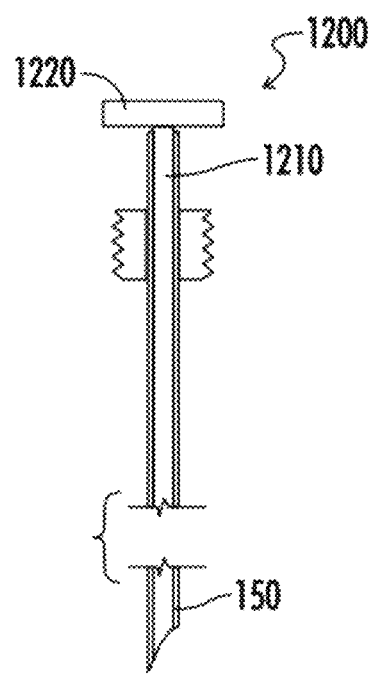

FIG. 12A illustrates an example of an application of a stylet 1100, preferably formed from a central solid core 1110 and an anchor 1120, with the hub 110 of FIG. 1A. More specifically, the diameter of the core 1110 is slightly smaller than the diameter of the lumen 151 of the needle 150 so that the core 1110 is able to travel through and fill the lumen 151 of the needle 150. When the needle 150 is punched into a lesion area (not shown), the core 1110 of the stylet 1100 prevents non-lesion tissue from entering the lumen 151 of the needle 150. Once the needle tip or inlet 153 reaches the target tissue (not shown), the core 1110 of the stylet 1100 is withdrawn from the needle lumen 151 and a vacuum source (not shown) is connected to the hub 110 and the needle 150 to aspirate the specimen at the target tissue. Thus, the stylet 1100 prevents the collection of an unwanted specimen, such as a lesion area through which the needle 150 must travel in order to reach a target tissue specimen area. FIG. 12B illustrates an alternative embodiment of a stylet 1200 having a core 1210 and an anchor 1220 that is attached to a needle 150 before the needle 150 is attached to a hub (not shown), while FIG. 12A illustrates the use of a stylet 1100 that is attached to the needle 150 after the needle 150 is attached to the hub 110.

Figure 13A:
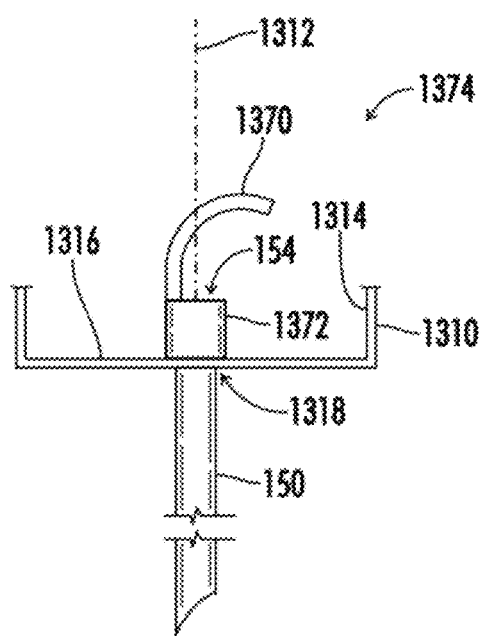
FIGS. 13A and 13B illustrate one embodiment of a device including a flexible cover.
Figure 13B:
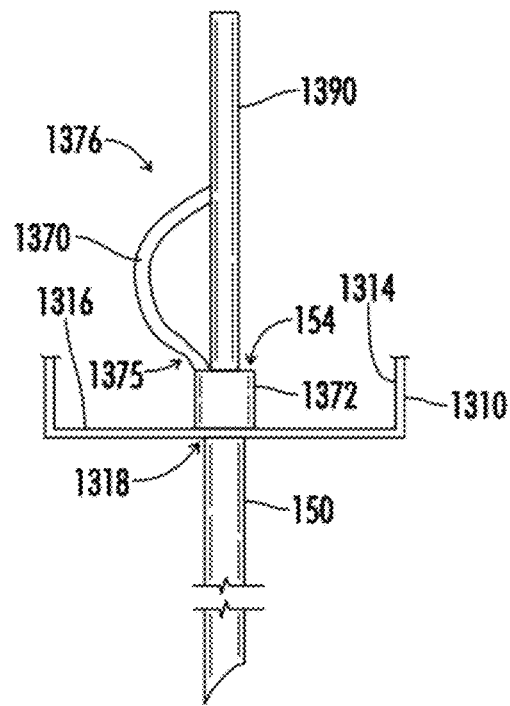
Figure 13C:
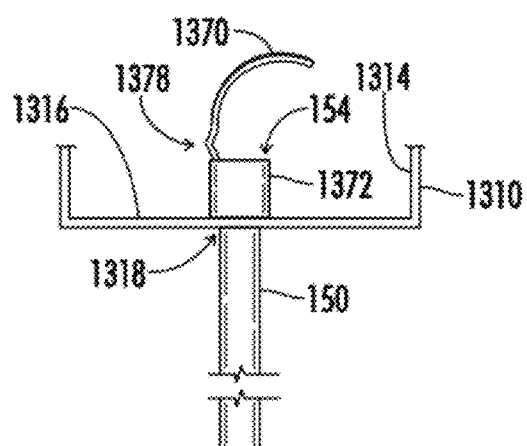
FIGS. 13C and 13D illustrate one embodiment of a device including a flexible cover having a hinge.
Figure 13D:
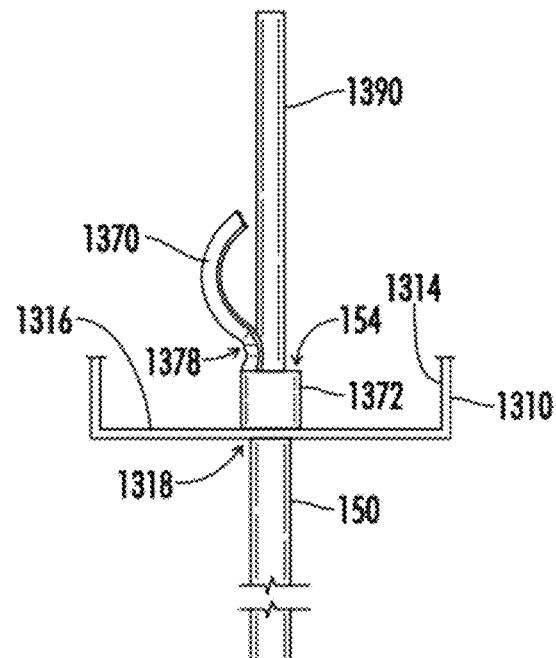

While FIG. 11-FIG. 12B illustrates the use of certain embodiments of a stylet 1100, 1200 engaged with a needle 150 that is not associated with a hub having a cover over the needle outlet, for the reasons described herein it is preferable in certain situations that a cover is used to direct a collected specimen toward the hub floor. In the alternative embodiments of FIG. 13A-FIG. 13D, there is provided a hub 1310 having a sidewall 1314, a floor 1316, a channel 1318 in the floor 1316 for extension of a needle 150, and a cover 1370 that attaches to or otherwise extends from the floor 1316 with a collar 1372 or the like to cover a needle outlet 154. The cover 1370 is preferably formed from a flexible material that allows the cover 1370 to move from a first position 1374 shown in FIG. 13A that extends over a portion of the needle outlet 154, to a second position 1376 shown in FIG. 13B away from the needle outlet 154, in response to, for example, the passage of a stylet 1390 through the needle 150. The cover 1370 may be formed from a flexible material throughout the extent of the body of the cover 1370, or it may be formed from a sturdier material throughout a majority of the body and a flexible material only in a location 1375 near the collar 1372. The cover 1370 may therefore bend at such location 1375 by virtue of the inherent properties of the material, or the cover 1370 may be provided with a hinge 1378 as shown in FIG. 13C that allows the cover 1370 to flex rearwardly as shown in the embodiment of FIG. 13D. The hinge 1378 may be formed from the same material as the cover 1370, or it may be a different material, or it may be the same material but with a reduced thickness. Other embodiments are possible. Thus, when it is desired to introduce a stylet 1390 into the lumen of the needle 150, the cover 1370, which is positioned over the longitudinal axis 1312 of the hub 1310, is moved back and away from the longitudinal axis 1312 of the hub 1310 to allow for the introduction of the stylet 1390 into the needle 150. When the stylet 1390 is removed from the needle 150, the cover 1370 returns to its original position as shown in FIG. 13A or FIG. 13C to extend over the longitudinal axis 1312 of the hub 1310 and function to cover the needle outlet 154 as described herein.

FIG. 14A-FIG. 17B illustrate various alternative embodiments that incorporate the use or association of a seal with a hub structure for maintaining the integrity of the hub chamber during and after collection of a specimen therein. In certain embodiments described herein, the seal is a layer of material that comprises certain material properties that enables it to be pierced to accommodate the penetration of or passage of a needle or a stylet therethrough, and once the needle and/or stylet is removed, the seal returns to its original state for sealing the location through which the needle or stylet was passed. In certain non-limiting embodiments, the seal is formed from, but not limited to, silicon, polymers, rubber and other materials that function as described.

Figure 14A:
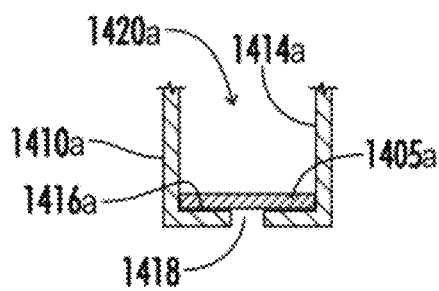
FIG. 14A illustrates one embodiment of a device hub including one embodiment of a seal.
Figure 14D:
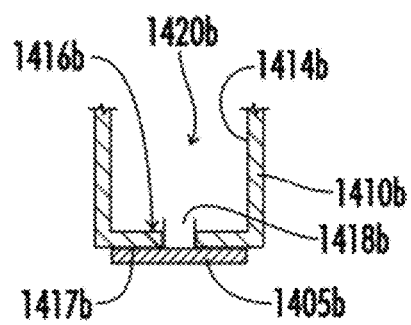
FIG. 14D illustrates one embodiment of a device hub including one embodiment of a seal.
Figure 14B:
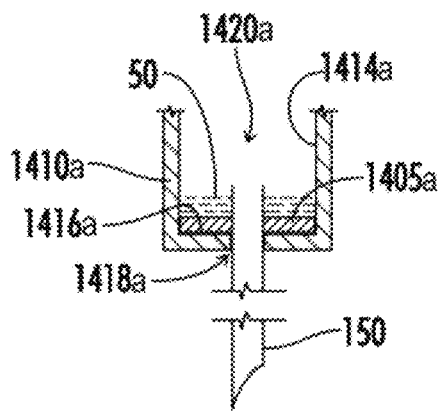
FIG. 14B illustrates one embodiment of a needle attached to the embodiment of the device hub of FIG. 14A.
Figure 14E:
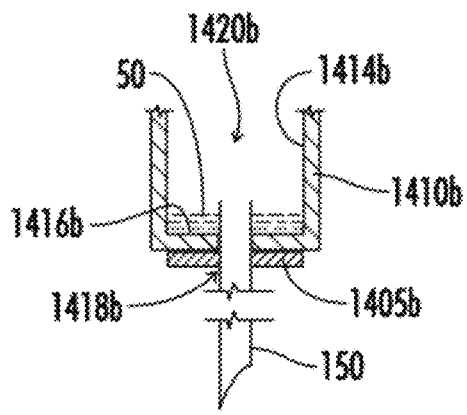
FIG. 14E illustrates one embodiment of a needle attached to the embodiment of the device hub of FIG. 14D.
Figure 14C:
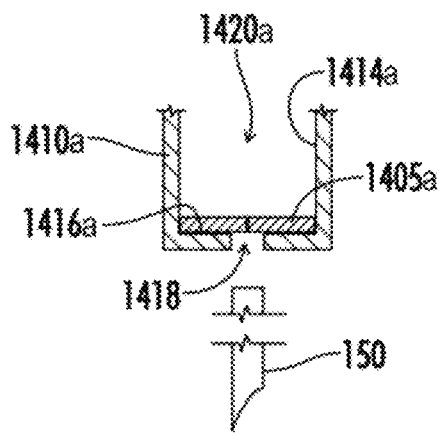
FIG. 14C illustrates the embodiment of the device hub of 14B with the needle removed.

FIG. 14A-FIG. 14C illustrate one embodiment of a hub 1410*a* (shown for purposes of explanation without a cover) having a sidewall 1414*a*, a floor 1416*a*, a channel 1418*a* that is flush with the floor 1416*a* for extension of a needle 150 (FIG. 14B) therethrough, a hub chamber 1420*a*, and a seal 1405*a* positioned on the floor 1416*a* and over the channel 1418*a*. The seal 1405*a* initially seals the hub chamber 1420*a* from the opening created by the channel 1418*a* (FIG. 14A) and is preferably attached to the floor 1416*a* by any means now known or hereinafter developed, such as by adhesives or the like. Alternatively, the seal 1405*a* may simply be removably inserted onto the floor 1416*a*. When a needle 150 is attached through the channel 1418*a* in the floor 1416*a* as shown in FIG. 14B, the needle 150 penetrates the seal 1405*a* and creates an opening in the hub chamber 1420*a*. Thereafter, the needle 150 is used to obtain a specimen 50 that collects on the seal 1405*a*. Once the specimen collection is complete, the needle 150 is withdrawn from the hub 1410*a* through the seal 1405*a* at which point the hub chamber 1420*a* is re-sealed relative to the channel 1418*a* as shown in FIG. 14C.

Figure 14F:
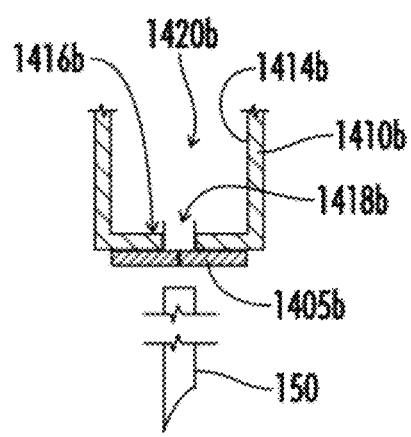
FIG. 14F illustrates the embodiment of the device hub of 14E with the needle removed.

FIG. 14D-FIG. 14F illustrate an alternate embodiment of a hub 1410*b* (shown for purposes of explanation without a cover) having a sidewall 1414*b*, a floor 1416*b*, a channel 1418*b* that extends through the floor 1416*b* for extension of a needle 150 (FIG. 14E) therethrough, a hub chamber 1420*b*, and a seal 1405*b* positioned on an undersurface 1417*b* of the hub 1410*b* adjacent the floor 1416*b* and over the channel 1418*b* as shown. The seal 1405*b* initially seals the hub chamber 1420*b* from the opening created by the channel 1418*b* (FIG. 14D) and is preferably attached to the undersurface 1417*b* by any means now known or hereinafter developed, such as by adhesives or the like. When a needle 150 is attached through the channel 1418*b* in the floor 1416*b* as shown in FIG. 14E, the needle 150 penetrates the seal 1405*b* and creates an opening in the hub chamber 1420*a*. Thereafter, the needle 150 is used to obtain a specimen 50 that collects on the hub floor 1416*b*. Once the specimen 50 collection is complete, the needle 150 is withdrawn from the hub 1410*b* through the seal 1405*b* at which point the hub chamber 1420*b* is re-sealed relative to the channel 1418*b* as shown in FIG. 14F.

Figure 14G:
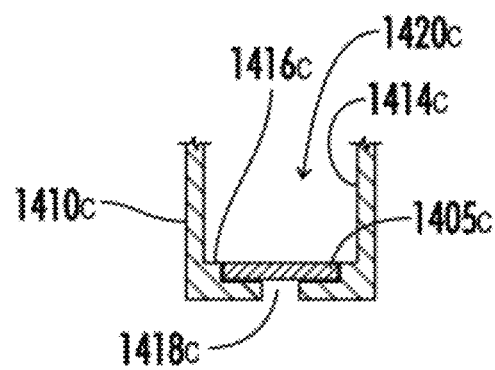
FIG. 14G illustrates one embodiment of a device hub including one embodiment of a seal.
Figure 14H:
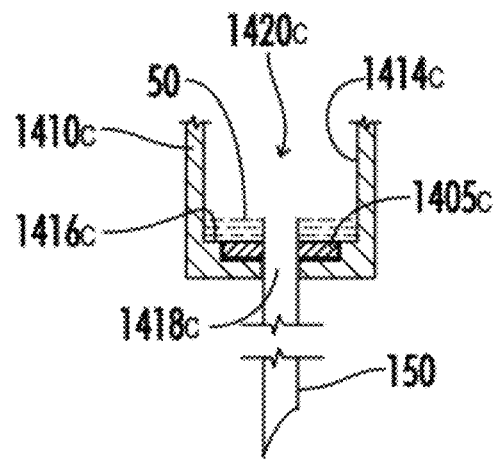
FIG. 14H illustrates one embodiment of a needle attached to the embodiment of the device hub of FIG. 14G.
Figure 14I:
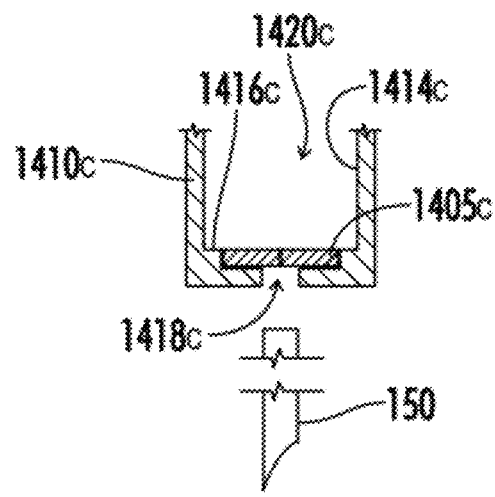
FIG. 14I illustrates the embodiment of the device hub of 14H with the needle removed.

In the embodiment of FIG. 14A-14F, the seal 1405*a*, 1405*b* is described as a separate element from the hub 1410*a*, 1410*b*. However, a seal may also be manufactured into a structure of the hub as shown in the embodiments of FIG. 14G-FIG. 14I, which illustrates an alternate embodiment of a hub 1410*c* (shown for purposes of explanation without a cover) having a sidewall 1414*c*, a floor 1416*c*, a channel 1418*c* in the floor 1416*c* for extension of a needle 150, a hub chamber 1420*c*, and a seal 1405*c* that is formed as part of the floor 1416*c*. The seal 1405*c* initially seals the hub chamber 1420*c* from the opening created by the channel 1418*c* (FIG. 14G). When a needle 150 is attached through the channel 1418*c* in the floor 1416*c* as shown in FIG. 14H, the needle 150 penetrates the seal 1405*c* and creates an opening in the hub chamber 1420*c*. Thereafter, the needle 150 is used to obtain a specimen 50 that collects on the hub floor 1416*c* and on the seal 1405*c*. Once the specimen 50 collection is complete, the needle 150 is withdrawn from the hub 1410*c* through the seal 1405*c* at which point the hub chamber 1420*c* is re-sealed relative to the channel 1418*c* as shown in FIG. 14I.

Figure 15A:
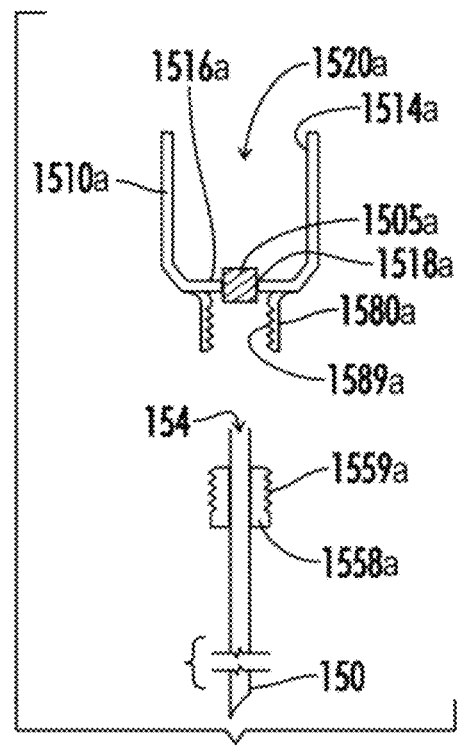
FIG. 15A illustrates one embodiment of a device hub including one embodiment of a seal.
Figure 15B:
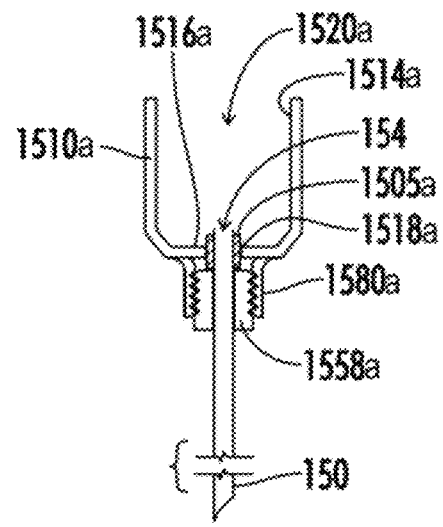
FIG. 15B illustrates one embodiment of a removable needle attached to the embodiment of the device hub of FIG. 15A.

FIG. 15A-FIG. 15B illustrate an alternate embodiment of a hub 1510*a* (shown for purposes of explanation without a cover) having a sidewall 1514*a*, a floor 1516*a*, a channel 1518*a* that extends through the floor 1516*a* for extension of a needle 150 therethrough, a hub chamber 1520*a*, and a seal 1505*a* that extends through the channel 1518*a* within the floor 1516*a*. The seal 1505*a* initially seals the hub chamber 1520*a* from the opening created by the channel 1518*a*. The needle 150 is preferably detachably connected to the hub 1510*a* through the engagement of a needle holder 1558*a* with a hub extension 1580*a*. More specifically, the needle holder 1558*a* is provided with an outer thread 1559*a* that engages an inner thread 1589*a* on the hub extension 1580*a*, wherein the needle outlet 154 penetrates through the seal 1505*a* and through the channel 1518*a* during engagement of the needle holder 1558*a* with the hub extension 1580*a* as shown in FIG. 15B. Thereafter, the needle 150 is used to obtain a specimen 50 that collects on the hub floor 1516*a*. Once the specimen 50 collection is complete, the needle 150 is removed from the hub 1510*a* at which point the hub chamber 1520*a* is re-sealed relative to the channel 1518*a*.

Figure 15C:
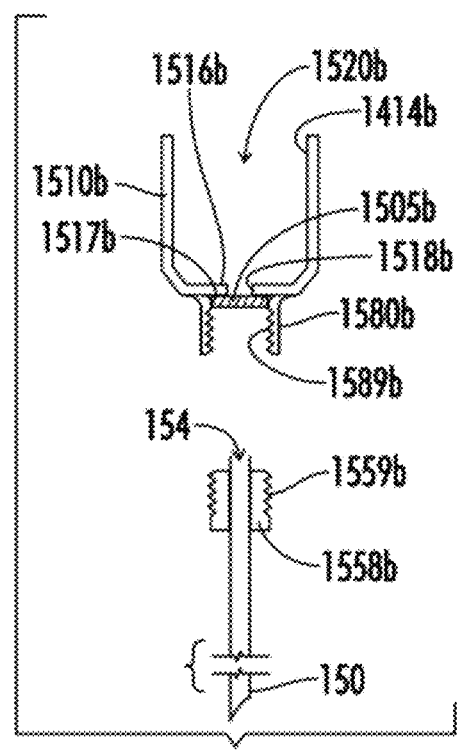
FIG. 15C illustrates one embodiment of a device hub including one embodiment of a seal.
Figure 15D:
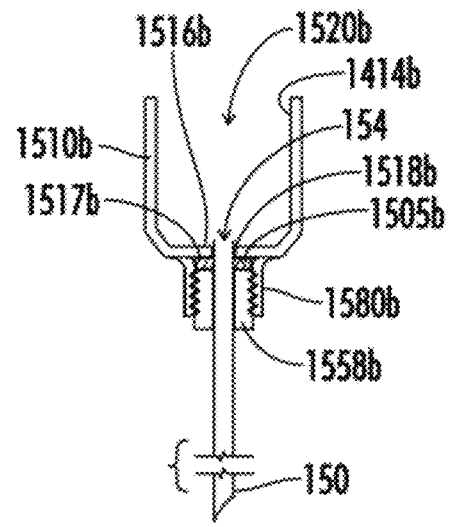
FIG. 15D illustrates one embodiment of a removable needle attached to the embodiment of the device hub of FIG. 15C.

FIG. 15C-FIG. 15D illustrate an alternate embodiment of a hub 1510*b* (shown for purposes of explanation without a cover) having a sidewall 1514*b*, a floor 1516*b*, a channel 1518*b* that extends through the floor 1516*b* for extension of a needle 150 therethrough, a hub chamber 1520*b*, and a seal 1505*b* that extends across the channel 1518*b* and is preferably attached to the undersurface 1517*b* of the hub 1510*b* within a hub extension 1580*b* by any means now known or hereinafter developed, such as by adhesives or the like. The seal 1505*b* initially seals the hub chamber 1520*b* from the opening created by the channel 1518*b*. The needle 150 is preferably detachably connected to the hub 1510*b* through the engagement of the needle holder 1558*b* with the hub extension 1580*b*. More specifically, the needle holder 1558*b* is provided with an outer thread 1559*b* that engages an inner thread 1589*b* on the hub extension 1580*b*, wherein the needle outlet 154 penetrates through the seal 1505*b* and through the channel 1518*b* during engagement of the needle holder 1558*b* with the hub extension 1580*b* as shown in FIG. 15D. Thereafter, the needle 150 is used to obtain a specimen 50 that collects on the hub floor 1516*b*. Once the specimen 50 collection is complete, the needle 150 is removed from the hub 1510*b* at which point the hub chamber 1520*b* is re-sealed relative to the channel 1518*b*.

Figure 15E:
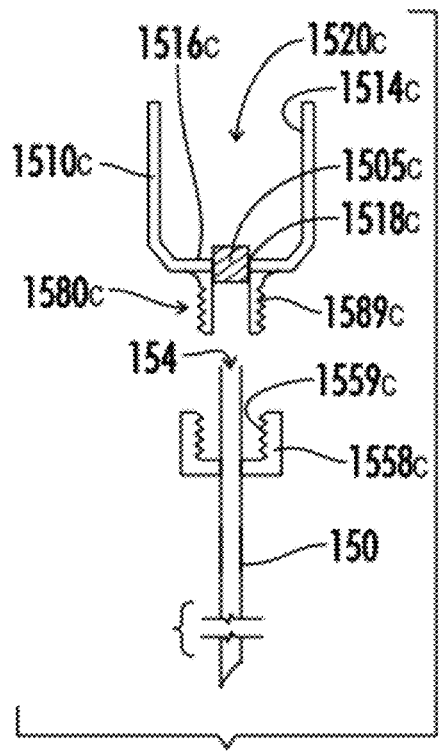
FIG. 15E illustrates one embodiment of a device hub including one embodiment of a seal.
Figure 15F:
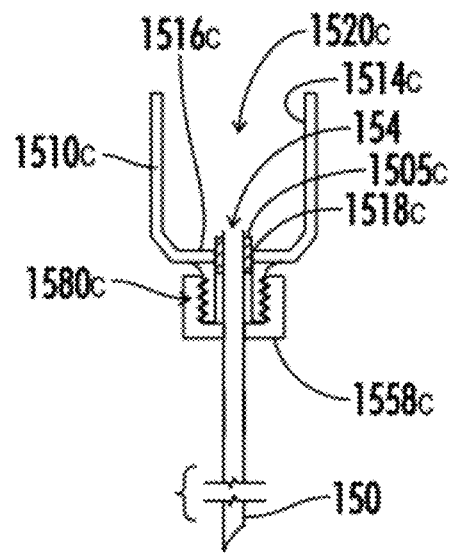
FIG. 15F illustrates one embodiment of a removable needle attached to the embodiment of the device hub of FIG. 15E.

FIG. 15E-FIG. 15F illustrate an alternate embodiment of a hub 1510c (shown for purposes of explanation without a cover) having a sidewall 1514c, a floor 1516c, a channel 1518c that extends through the floor 1516c for extension of a needle 150 therethrough, a hub chamber 1520c, and a seal 1505c that extends through the channel 1518c within the floor 1516c. The seal 1505c initially seals the hub chamber 1520c from the opening created by the channel 1518c. The needle 150 is preferably detachably connected to the hub 1510c through the engagement of a needle holder 1558c with a hub extension 1580c. More specifically, the needle holder 1558c is provided with an inner thread 1559c that engages an outer thread 1589c on the hub extension 1580c, wherein the needle outlet 154 penetrates through the seal 1505c and through the channel 1518c during engagement of the needle holder 1558c with the hub extension 1580c as shown in FIG. 15F. Thereafter, the needle 150 is used to obtain a specimen 50 that collects on the hub floor 1516c. Once the specimen 50 collection is complete, the needle 150 is removed from the hub 1510c at which point the hub chamber 1520c is re-sealed relative to the channel 1518c.

Figure 15G:
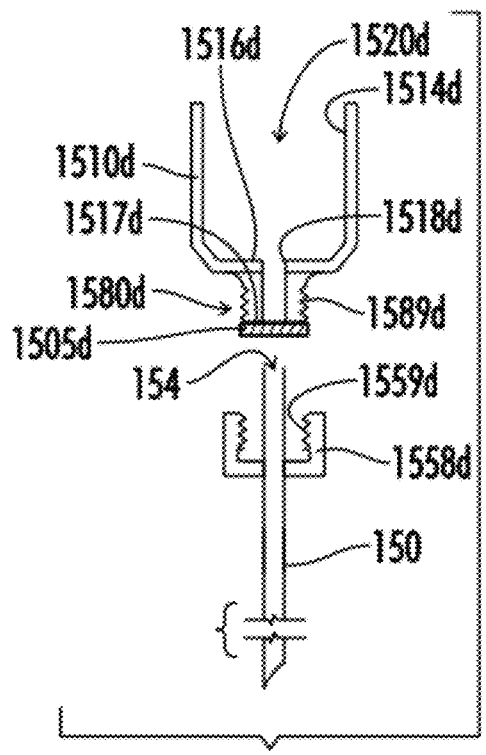
FIG. 15G illustrates one embodiment of a device hub including one embodiment of a seal.
Figure 15H:
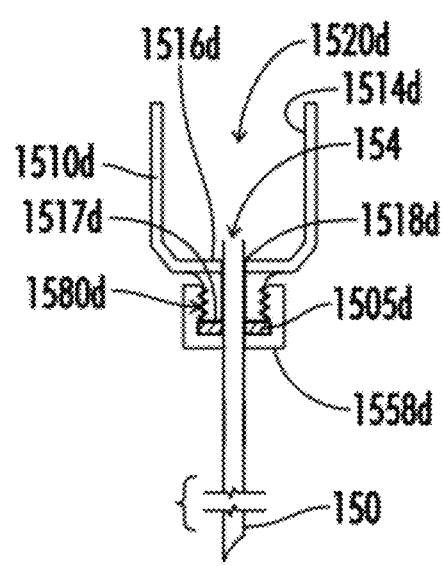
FIG. 15H illustrates one embodiment of a removable needle attached to the embodiment of the device hub of FIG. 15G.

FIG. 15G-FIG. 15H illustrate an alternate embodiment of a hub 1510d (shown for purposes of explanation without a cover) having a sidewall 1514d, a floor 1516d, a channel 1518d that extends through the floor 1516d for extension of a needle 150 therethrough, a hub chamber 1520d, and a seal 1505d that extends across the channel 1518d and is preferably attached to the undersurface 1517d of the hub 1510d across a hub extension 1580d by any means now known or hereinafter developed, such as by adhesives or the like. The seal 1505d initially seals the hub chamber 1520d from the opening created by the channel 1518d. The needle 150 is preferably detachably connected to the hub 1510d through the engagement of a needle holder 1558d with the hub extension 1580d. More specifically, the needle holder 1558d is provided with an inner thread 1559d that engages an outer thread 1589d on the hub extension 1580d, wherein the needle outlet 154 penetrates through the seal 1505d and through the channel 1518d during engagement of the needle holder 1558d with the hub extension 1580d as shown in FIG. 15H. Thereafter, the needle 150 is used to obtain a specimen 50 that collects on the hub floor 1516d. Once the specimen 50 collection is complete, the needle 150 is removed from the hub 1510d at which point the hub chamber 1520d is re-sealed relative to the channel 1518d.

Figure 16A:
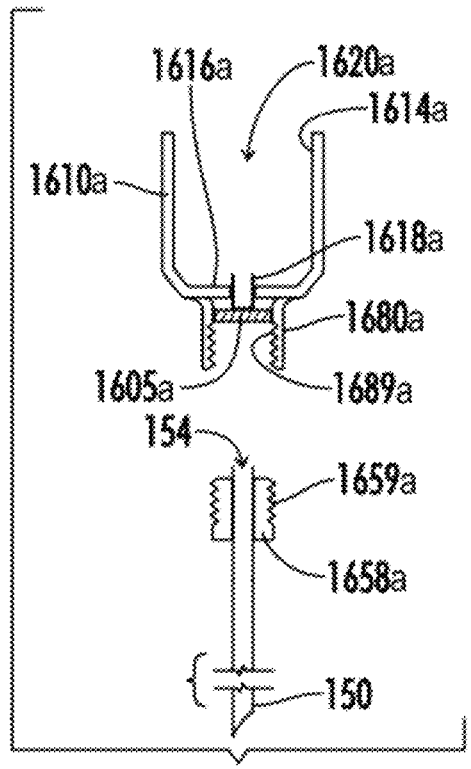
FIG. 16A illustrates one embodiment of a device hub including one embodiment of a seal.
Figure 16B:
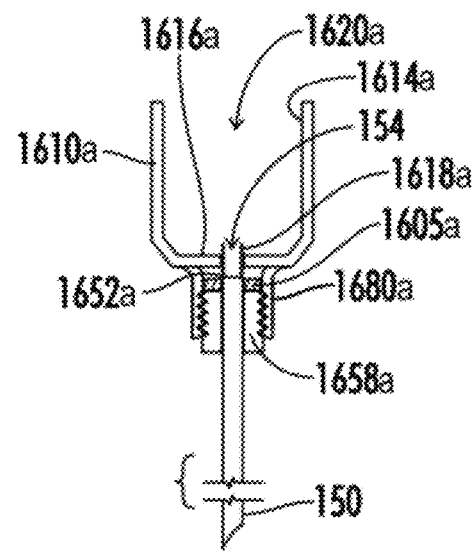
FIG. 16B illustrates one embodiment of a removable needle attached to the embodiment of the device hub of FIG. 16A.

In the embodiment of FIG. 14A-15H, the needle 150 has a diameter that is less than the diameter of the hub channel, such that the needle outlet 154 extends through the hub channel and into the hub chamber. However, consistent with the previously-described embodiment of FIG. 11, the needle and the hub channel may have the same diameter such that they join in an abutting relationship. Thus, for example, the embodiment of FIG. 16A-FIG. 16B illustrate an alternate embodiment of a hub 1610a (shown for purposes of explanation without a cover) similar to the hub 1520b of FIG. 15C-15D, but where the needle 150 has a diameter that is the same as the diameter of the hub channel 1618a such that the needle 150 and channel 1618a abut at a junction point 1652a to form a single unified lumen. More specifically, the hub 1610a has a sidewall 1614a, a floor 1616a, a channel 1618a that extends through the floor 1616a, a hub chamber 1620a, and a seal 1605a that extends across the channel 1618a and is preferably attached to an undersurface 1617a of the hub 1610a within a hub extension 1680a by any means now known or hereinafter developed, such as by adhesives or the like. The seal 1605a initially seals the hub chamber 1620a from the opening created by the channel 1618a. The needle 150 is preferably detachably connected to the hub 1610a through the engagement of the needle holder 1658a with the hub extension 1680a. More specifically, the needle holder 1658a is provided with an outer thread 1659a that engages an inner thread 1689a on the hub extension 1680a, wherein the needle outlet 154 penetrates through the seal 1605a and abuts the channel 1618a at a joint location 1652a during engagement of the needle holder 1658a with the hub extension 1680a as shown in FIG. 16B. Thereafter, the needle 150 is used to obtain a specimen 50 that collects on the hub floor 1616a. Once the specimen 50 collection is complete, the needle 150 is removed from the hub 1610a at which point the hub chamber 1620a is re-sealed relative to the channel 1618a.

Figure 16C:
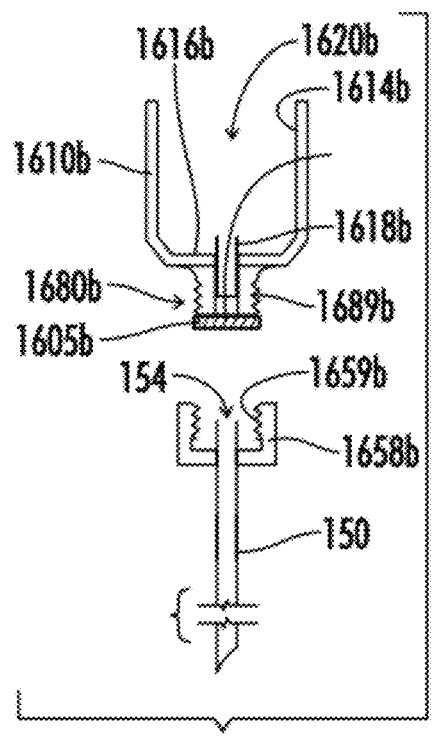
FIG. 16C illustrates one embodiment of a device hub including one embodiment of a seal.
Figure 16D:
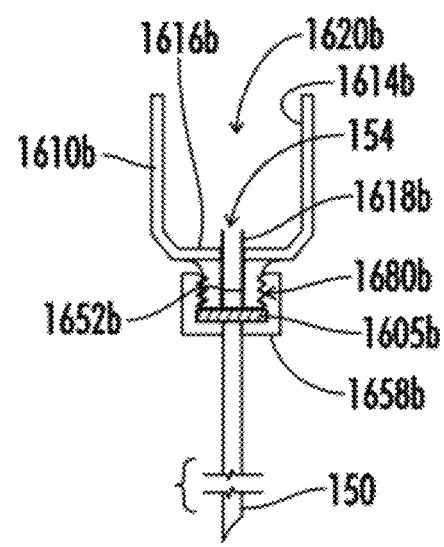
FIG. 16D illustrates one embodiment of a removable needle attached to the embodiment of the device hub of FIG. 16C.

Similar to the embodiment of FIG. 15G-15H, the embodiment of FIG. 16C-FIG. 16D illustrate an alternate embodiment of a hub 1610b (shown for purposes of explanation without a cover) having a sidewall 1614b, a floor 1616b, a channel 1618b that extends through the floor 1616b, a hub chamber 1620b, and a seal 1605b that extends across the channel 1618b and is preferably attached to the undersurface 1617b of the hub 1610b across a hub extension 1680b by any means now known or hereinafter developed, such as by adhesives or the like. The seal 1605b initially seals the hub chamber 1620b from the opening created by the channel 1618b. The needle 150 is preferably detachably connected to the hub 1610b through the engagement of a needle holder 1658b with the hub extension 1680b. More specifically, the needle holder 1658b is provided with an inner thread 1659b that engages an outer thread 1689b on the hub extension 1680b, wherein the needle outlet 154 penetrates through the seal 1605b and abuts the channel 1618b at a joint location 1652b during engagement of the needle holder 1658b with the hub extension 1680b as shown in FIG. 16D. Thereafter, the needle 150 is used to obtain a specimen 50 that collects on the hub floor 1616b. Once the specimen 50 collection is complete, the needle 150 is removed from the hub 1610b at which point the hub chamber 1620b is re-sealed relative to the channel 1618b.

In the embodiment of FIG. 17A-17B, there is provided an alternative embodiment of a multifunction aspiration biopsy device 1700 that is combined with a method of incorporating and delivering a stylet 1790 to a specimen site (not shown). Conventional aspiration needles may be composed of two distinct parts, namely a needle with stylet and a vacuum source (such as a syringe), which are generally packaged separately from each other. During a typical procedure, a practitioner (such as a physician) first introduces the needle with the stylet into a patient's body and reaches the target area (the lesion area), then the stylet is drawn out from the needle, and then the needle is connected with the vacuum source to draw out the cells and tissue from the target area. This process may cause some difficulty and inconvenience for the practitioner and additional discomfort to the patient due to the step of connecting the needle to the vacuum source when the needle is inside the patient. However, in the embodiment of FIG. 17A-17B, the needle and vacuum source work together as a single unit when the needle is introduced into the patient's body and when the stylet is withdrawn from the needle, thus overcoming the above-described difficulty and inconvenience to the practitioner and patient.

More specifically, FIG. 17A-17B illustrates an alternative embodiment of a multifunction aspiration biopsy device 1700 in combination with a stylet 1790, the multifunction aspiration biopsy device 1700 having a hub 1710 with a longitudinal axis 1712 and a sidewall 1714 extending to a floor 1716 to form a chamber 1720. The floor 1716 has a channel 1718 bounded by channel walls 1719 that form a passage for the needle 150. While the sidewall 1714 is shown with a consistent diameter, for example, it will be appreciated that other configurations are possible, such as, but not limited to a tapered sidewall as shown, for example, in the embodiment of FIG. 2. Other configurations are possible. Device 1700 also comprises a vacuum source 1730 in communication with the chamber 1720, a needle 150 having an inner lumen 151 detachably extending along the longitudinal axis 1712 of the hub 1710 through the channel walls 1719 of the channel 1718 in the floor 1716 and having a needle inlet 153 and a needle outlet 154 along the longitudinal axis 1712 and in communication with the hub chamber 1720, and a cover 1770 extending over a portion of the needle outlet 154 along a second axis 1752 that differs from the longitudinal axis 1712 for directing a specimen 50 collected through the needle 150 into the chamber 1720 in a direction that differs from the longitudinal axis 1712. The vacuum source 1730 further comprises a barrel 1732 and a plunger 1734 movable within the barrel 1732. The barrel 1732 further comprises a sidewall 1736 having a threaded end 1737 that engages a threaded end 1717 of the sidewall 1714 of the hub 1710, and a barrel floor 1738 that limits movement of the plunger 1734 relative to the barrel 1732, the barrel floor 1738 and barrel sidewall 1736 defining a barrel chamber 1740. The barrel floor 1738 further comprises at least one opening 1739, and preferably a plurality of openings 1739 for communication between the barrel chamber 1740 and the hub chamber 1720. While, FIG. 17A-FIG. 17B show a threaded engagement between the hub 1720 and vacuum source 1730, other methods of engagement are possible.

In order to accommodate the stylet 1790 within the device 1700, seals 1705-1707 are strategically positioned in certain locations along the device 1700, preferably along the longitudinal axis 1712, including a cover seal 1705, a plunger body seal 1706 and a plunger handle seal 1707 that collectively accommodate the passage of a stylet 1790 as shown in FIG. 17B. Thus, a sealed pathway is created for the stylet 1790 through the vacuum source 1730 and through the hub 1710 so that the stylet 1790 can be directly connected to the needle 150 through the vacuum source 1730 and function as a single unit. After the stylet 1790 is introduced into a patient (not shown) and arrives at a target (i.e. lesion) area, the stylet 1790 is removed from the device 1700 and is withdrawn through the seals 1705-1707, whereupon the withdrawal of the stylet 1790 through the seal 1705 prevents any target cells and tissue present on the inserted end of the stylet 1790 from passing through the cover 1770 and into the vacuum source 1730. The seals 1706 and 1707 do not destroy the integrity of the vacuum and thus the vacuum source 1730 functions adequately when the stylet 1790 is not extended through the seals 1705-1707 as shown in FIG. 17A. Thus, with the embodiment of the device 1700 of FIG. 17A-17B, the needle 150 and vacuum source 1730 work together as a single unit when the needle 150 is introduced into the patient's body (not shown) and when the stylet 1790 is withdrawn from the needle 150, thus overcoming the above-described difficulties and inconvenience to the practitioner and patient.

Figure 18:
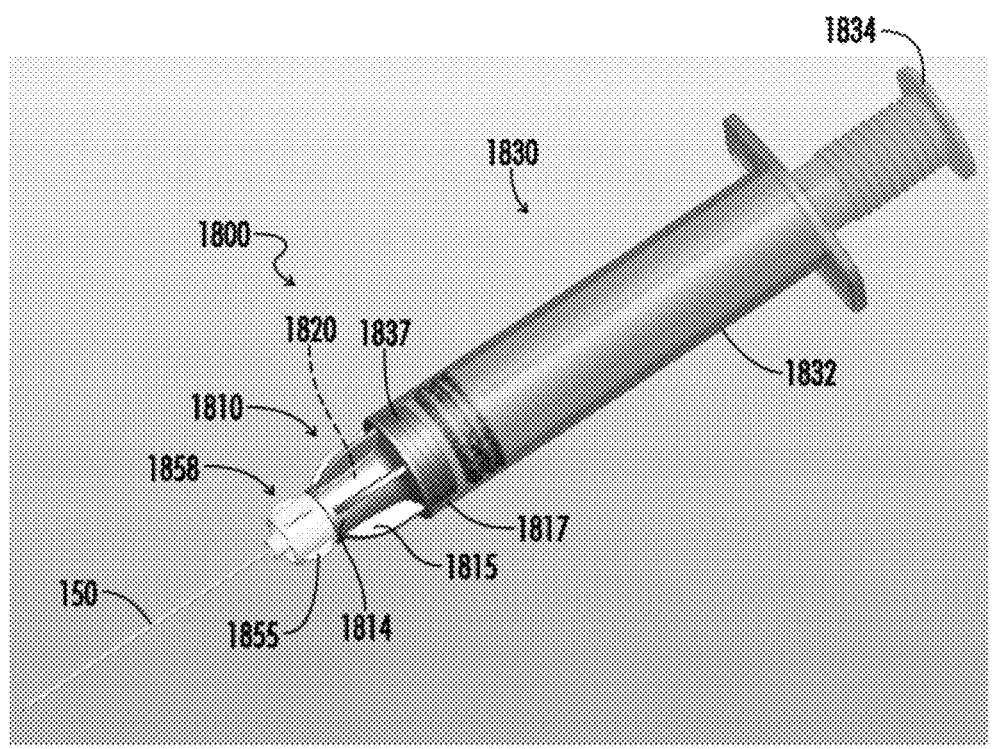
FIG. 18 illustrates an alternative embodiment of a multifunction aspiration biopsy device of the invention.

FIG. 18 illustrates a perspective view of one embodiment of a multifunction aspiration biopsy device 1800 having a hub 1810, an internal hub chamber 1820 for the collection of a specimen (not shown), a vacuum source 1830 defined by a barrel 1832 and a plunger 1834, and a needle 150 held by a needle holder 1858 that is removably attached to a hub extension (not shown) extending from the hub 1810. The sidewall 1814 of the hub 1810 terminates in an external thread 1817 that threadingly engages an internal thread 1837 on the barrel 1832 so that the hub 1810 is removable from the barrel 1832 as previously described in many embodiments herein. The sidewall 1814 of the hub is provided with at least one and more preferably a plurality of extensions or wings 1815 for improved gripping and for engagement with a sharps box as will be described below. The needle holder 1858 is also provided with at least one and more preferably a plurality of extensions or wings 1855 for improved gripping and for engagement with one embodiment of a collection container 1900 as described in connection with FIG. 19A-FIG. 19I below. The hub extensions 1815 extend outwardly a greater diameter than the needle holder extensions 1855, however the hub extensions 1815 may also extend outwardly at the same or at a lesser diameter than the needle holder extensions 1855. While the embodiment of FIG. 18 illustrates a certain number of extensions 1815, 1855, it will be appreciated that any number, size, diameter or other configuration may be possible.

Figure 19A:
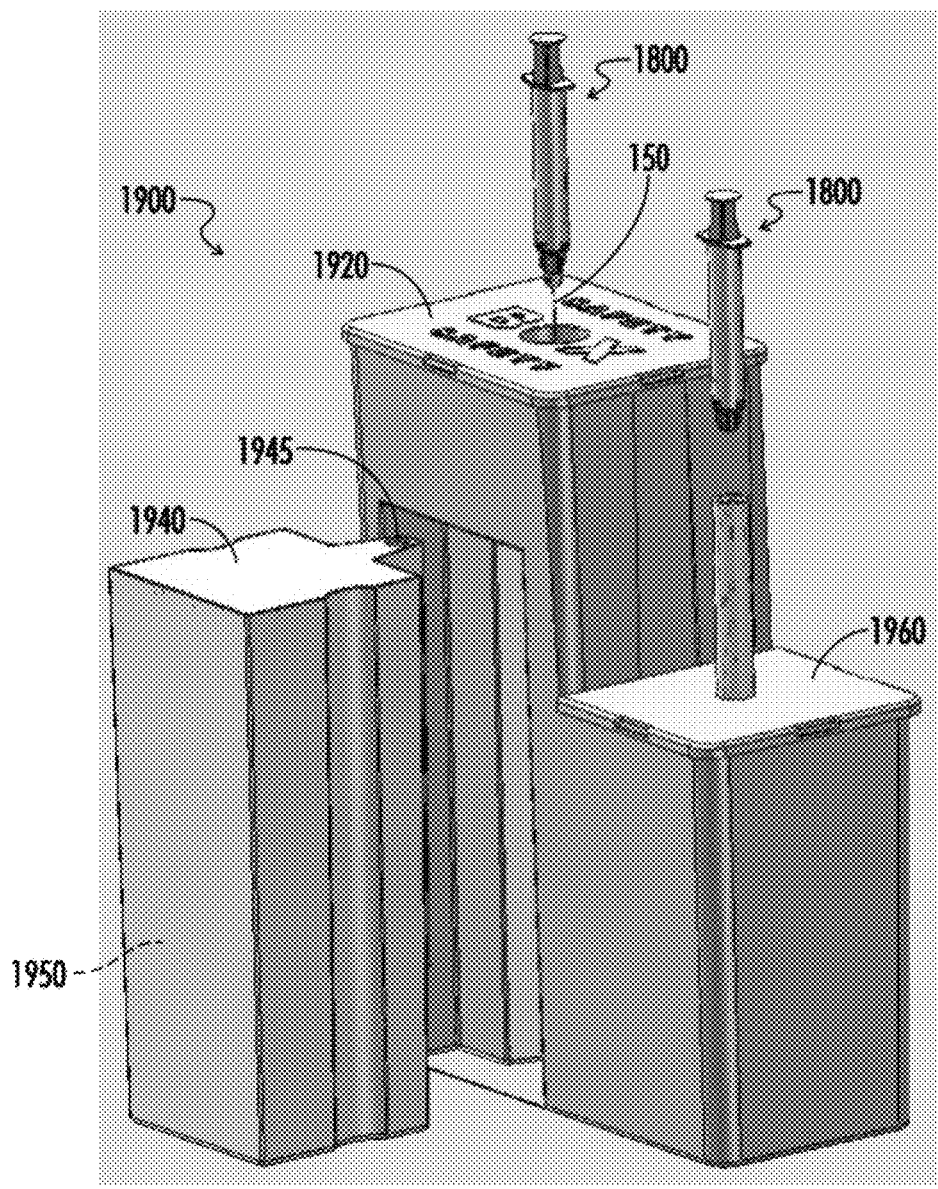
FIG. 19A illustrates an exploded view of one embodiment of a collection container shown assembled in the embodiment of FIG. 19B.
Figure 19B:
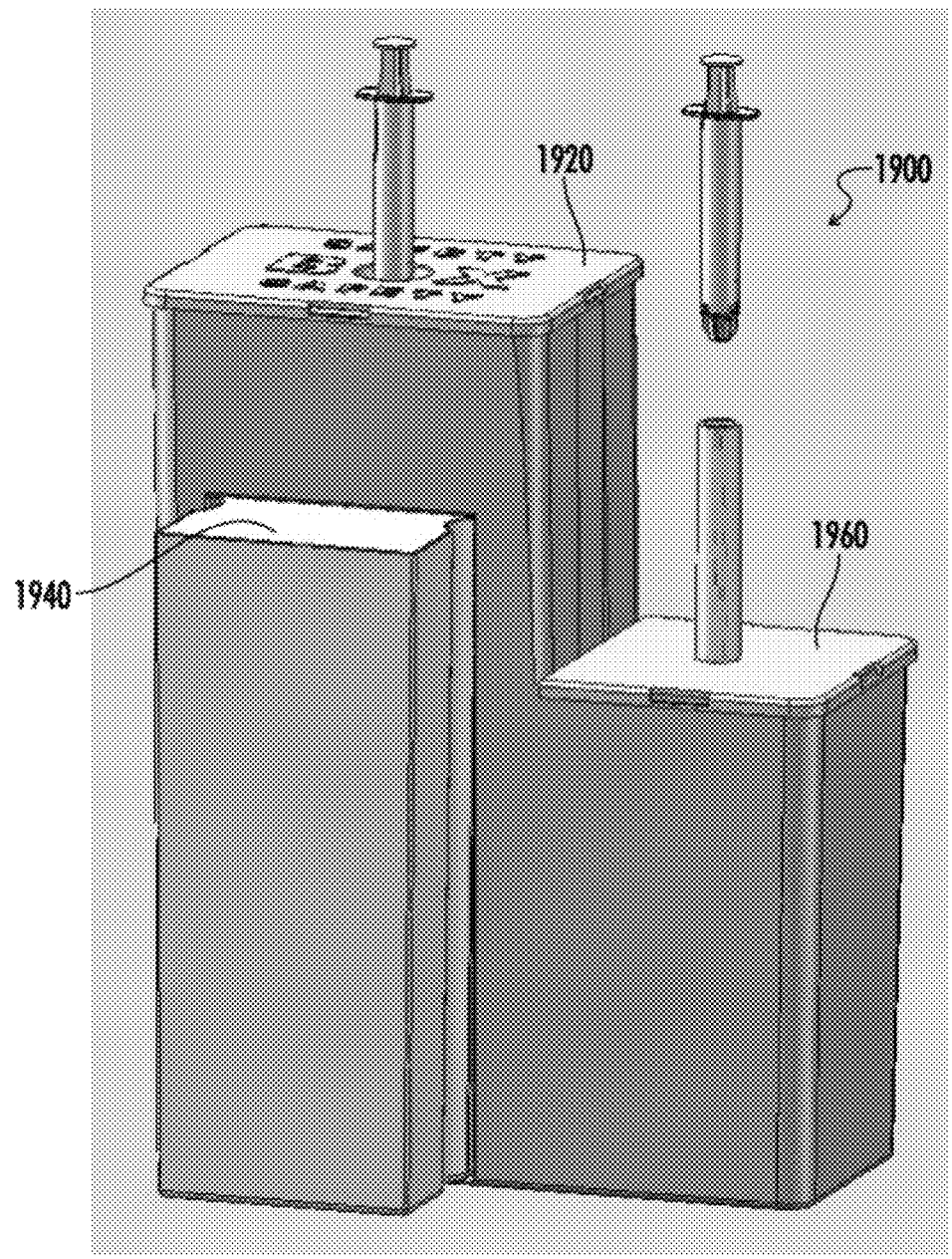
FIG. 19B shows an assembled view of the embodiment of a collection container shown exploded in FIG. 19A.
Figure 19C:
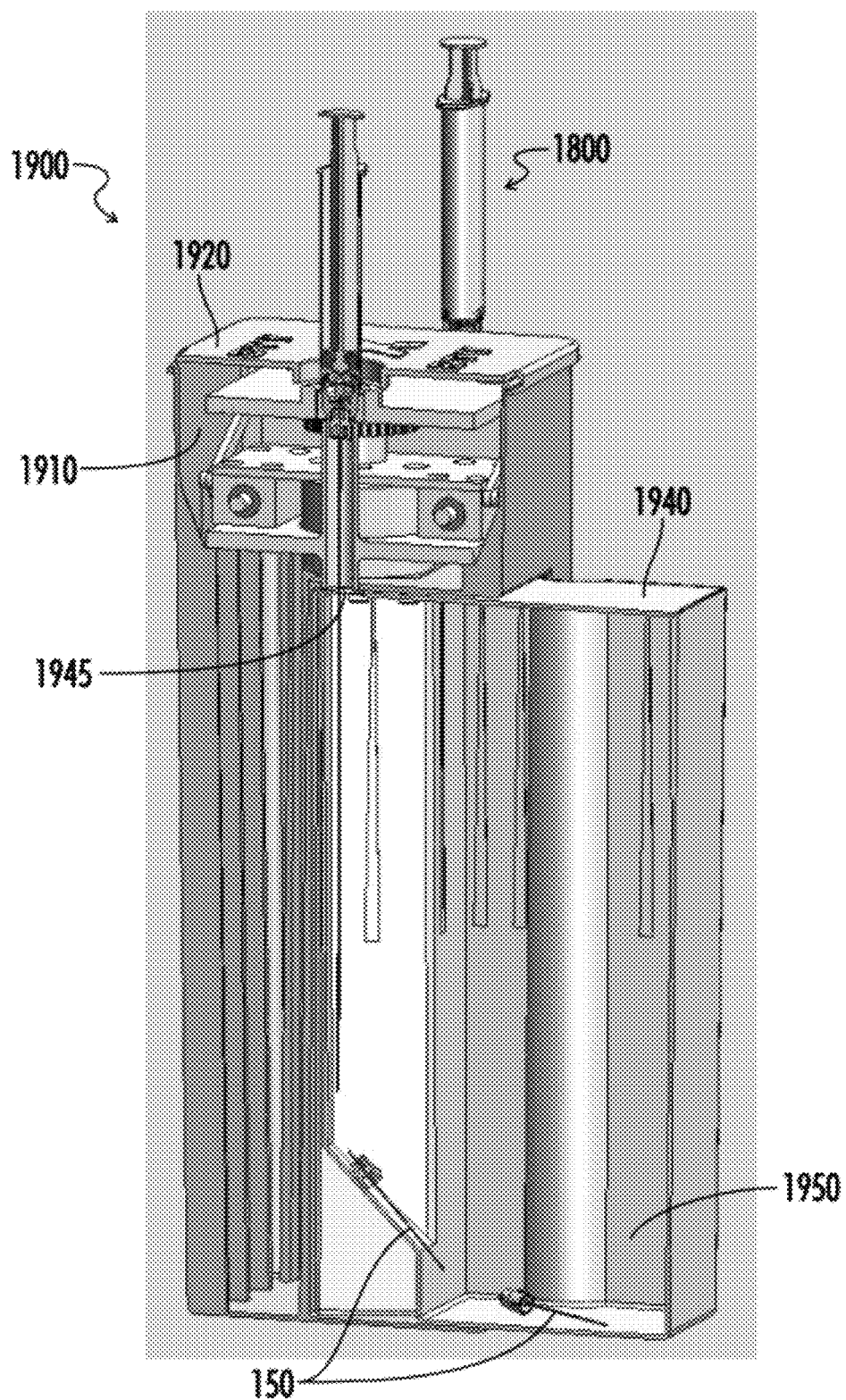
FIG. 19C illustrates a partial cross-section of the embodiment of the container of FIG. 19B.

FIG. 19A is an exploded view, FIG. 19B is an assembled view, and FIG. 19C is a partial cross-section of one embodiment of a collection container 1900 having a first component 1920 that is adapted to receive a multifunction aspiration biopsy device 1800 having an attached needle 150, a second component 1940 having an opening 1945 for the passage of used needles 150 and an interior 1950 for the collection of used needles 150, the second component 1940 preferably being removable from the first component 1920, and a third component 1960 that is adapted to plug a multifunction aspiration biopsy device 1800 as described herein. While multifunction aspiration biopsy device 1800 is used herein for purposes of explaining the construction and use of the collection container 1900, it will be appreciated that the container 1900 may be used with other biopsy devices or needles as desired. Furthermore, while container 1900 is described in connection with three components 1920, 1940 and 1960, it will be appreciated from the description below that the third component 1960 is optional, and that the second component 1940 may not be removable from the first component 1920. Other constructional variations are possible.

Figure 19D:
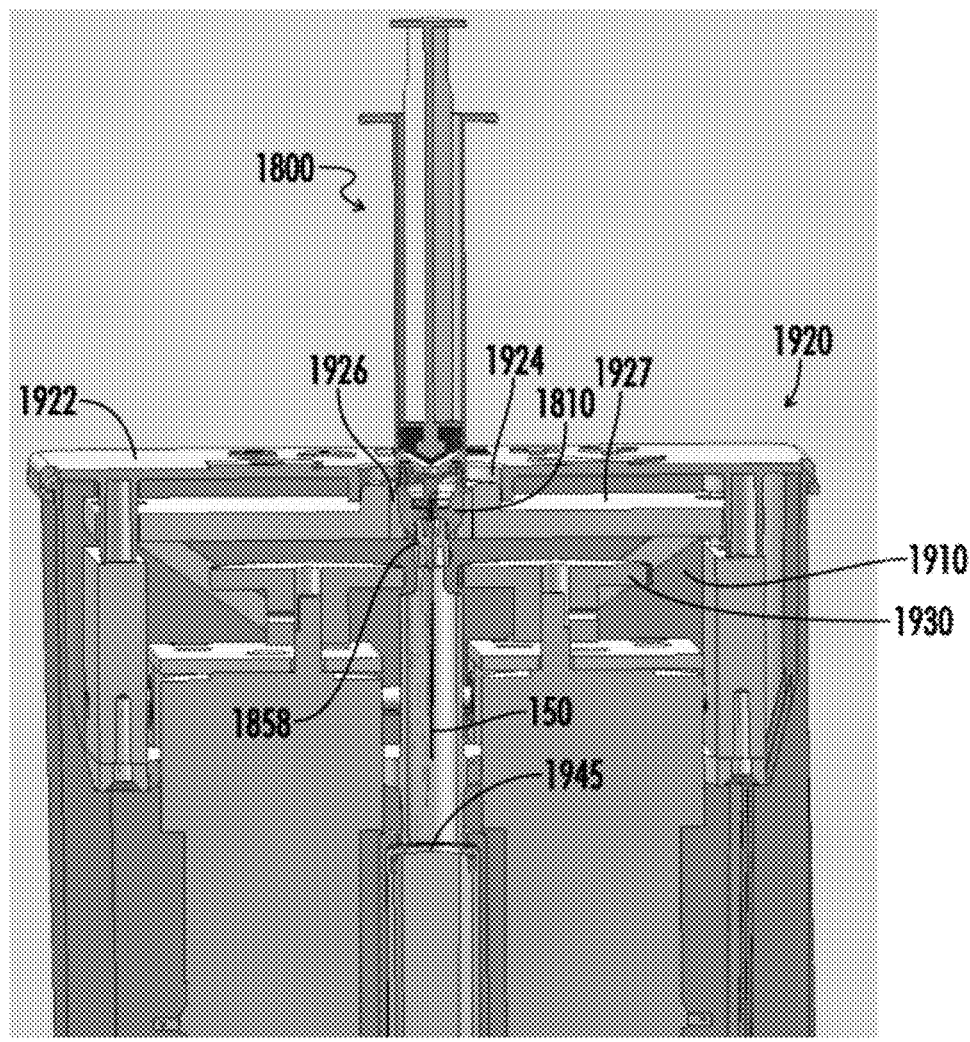
FIG. 19D illustrates a partial cross-section of the embodiment of the container of FIG. 19B.
Figure 19E:
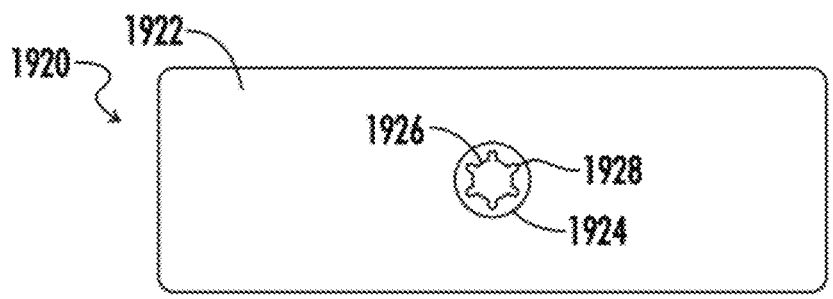
FIG. 19E illustrates one embodiment of a top view of a component of the container of FIG. 19B.
Figure 19F:
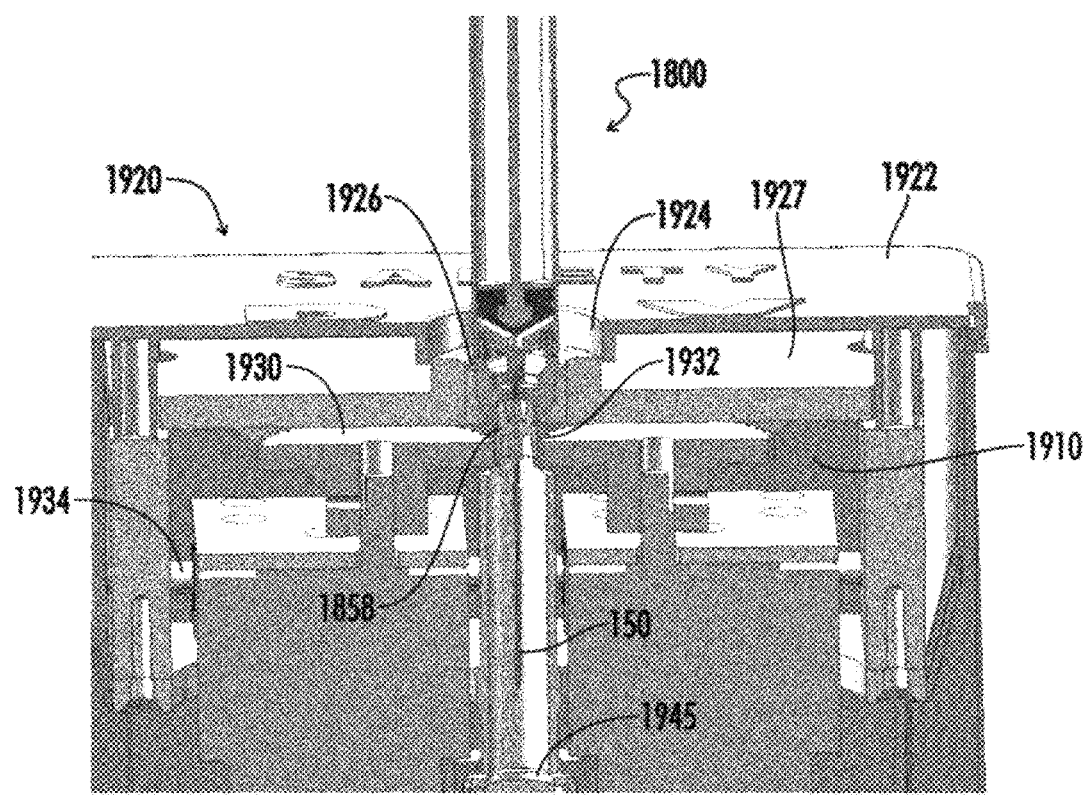
FIG. 19F illustrates a partial cross-section of the embodiment of the container of FIG. 19D.
Figure 19G:
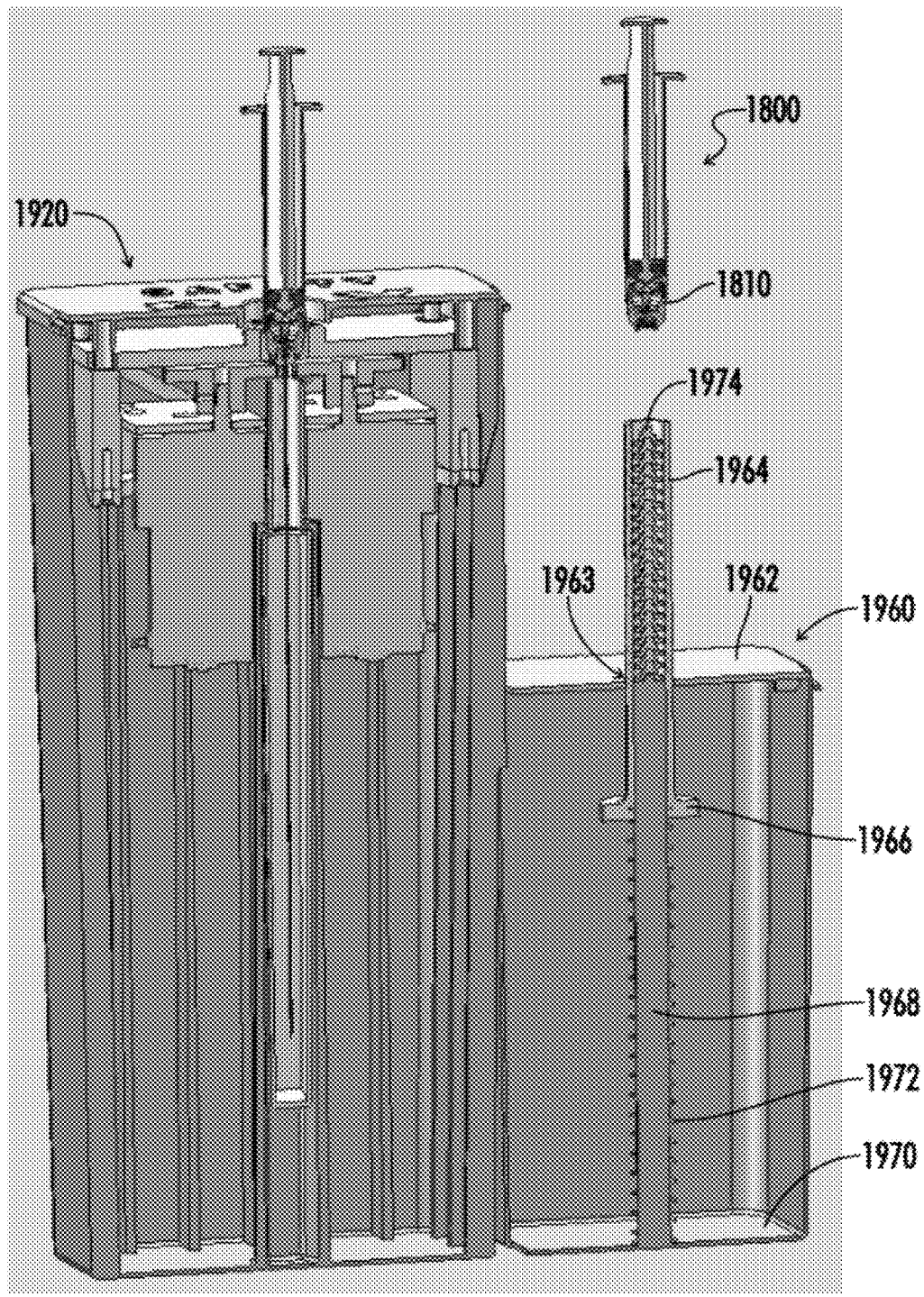
FIG. 19G illustrates a partial cross-section of one embodiment of the container of FIG. 19B.

FIG. 19D is a partial cross-section of one embodiment of the engagement of the device 1800 with the first component 1920 of the container 1900, the first component having an outer surface 1922, a first opening 1924 in the outer surface 1922 that is adapted to guide the device hub 1810 into a second opening 1926 provided on a support arm 1927, the second opening 1926 having slots 1928 (shown more clearly in the top view of the first component 1920 of FIG. 19E) that engage and capture the wings 1815 on the hub 1810 (see FIG. 18). The second opening 1926 is fixed within the support arm 1927 in the interior 1910 of the first component 1920 and functions to anchor the hub 1810 relative to the remainder of the device 1800 and relative to the needle holder 1858.

The first component 1920 of the container 1900 further comprises at least one and preferably a pair of gears 1930 having teeth 1932 that engage the wings 1855 (FIG. 18) on the needle holder 1858. The gears 1930 are movable along a support 1934 (FIG. 19F) between a first position shown in FIG. 19D that is spaced from an inserted needle holder 1858 to allow for insertion of the needle holder 1858 into the interior 1910 of the first component 1920, and a second position shown in FIG. 19F that is engaged with the needle holder 1858. Upon insertion of the device hub 1810 into the second opening 1926 and, in one embodiment, upon further pressing of the hub 1810 into the second opening 1926 which causes the support arm 1927 to be displaced downward, a switch (not shown) is activated that causes the gears 1930 to approach the needle holder 1858 so that the gear teeth 1932 engage the wings 1855 (FIG. 18) on the needle holder 1858 and then rotate the needle holder 1858 relative to the captured hub 1810 until the needle holder 1858 with needle 150 separates from the hub 1810 and drops through the opening 1945 and into the interior 1950 of the second component 1940 (see FIG. 19C). A power source and a drive mechanism (both not shown) may be incorporated into the container 1900 to power and drive the gears 1930.

Figure 20:
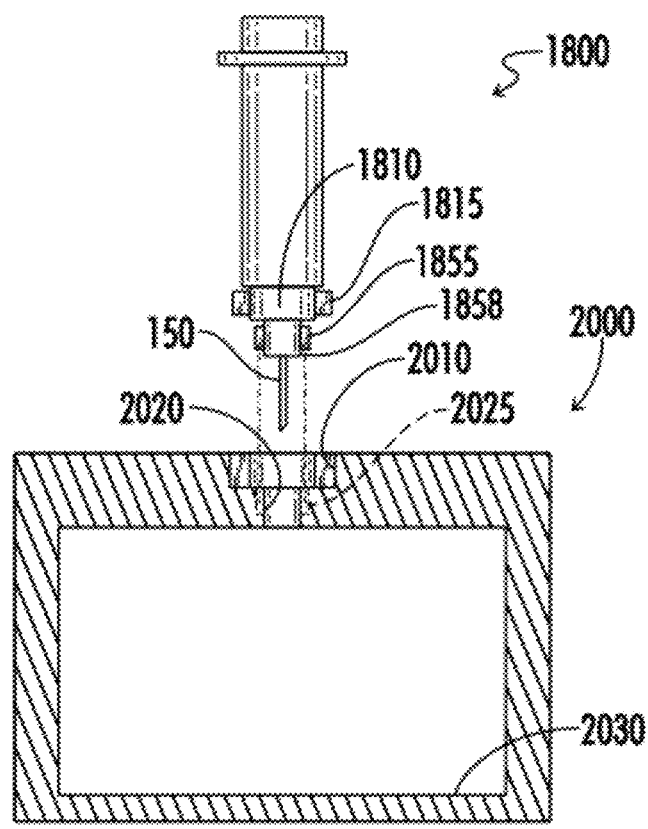
FIG. 20 illustrates one embodiment of a manually-operated collection container.
Figure 21A:
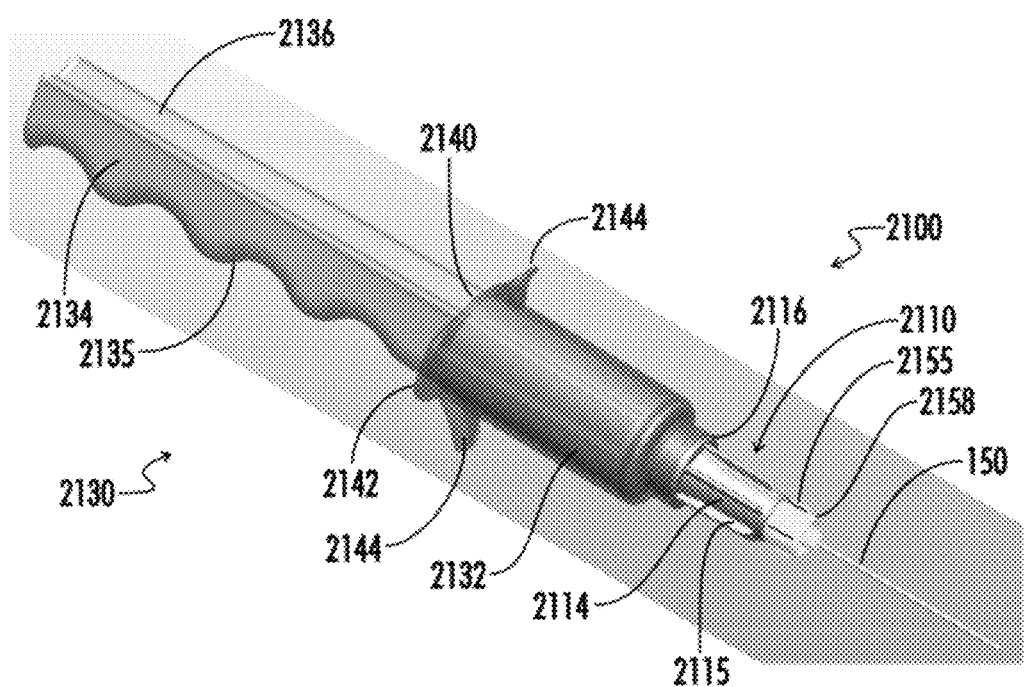
FIG. 21A illustrates an alternative embodiment of a multifunction aspiration biopsy device of the invention.
Figure 21C:
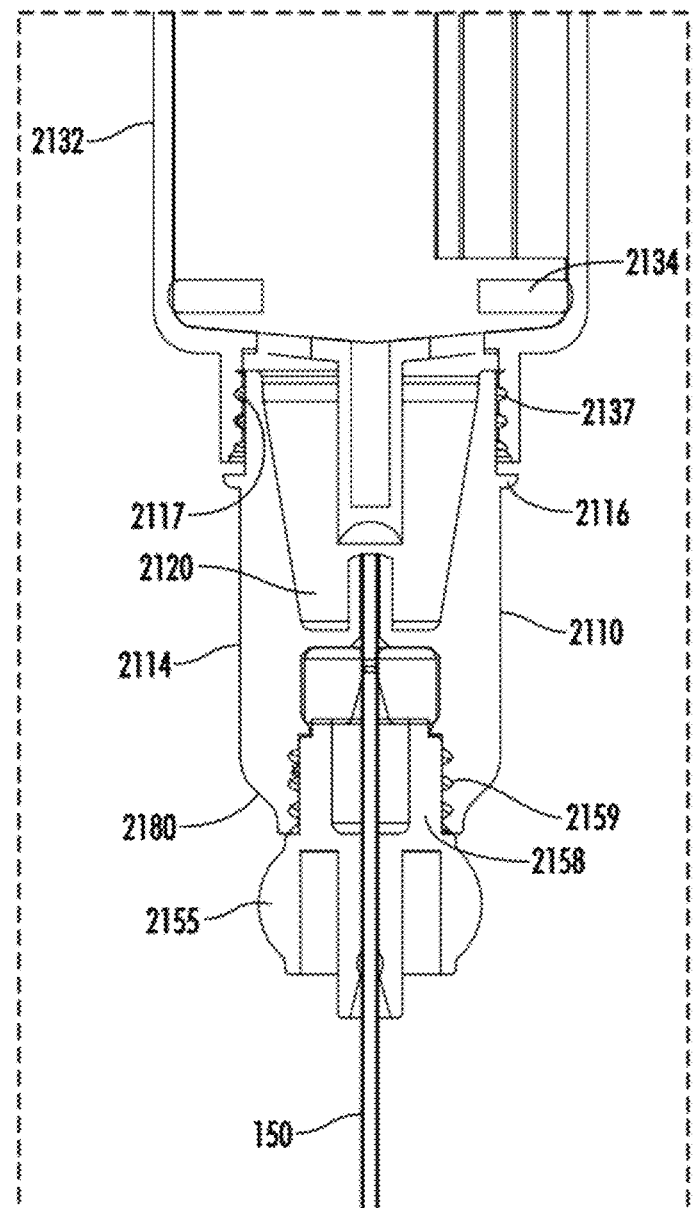
FIG. 21C illustrates a close-up view of the area 21C of FIG. 21B.
Figure 21D:
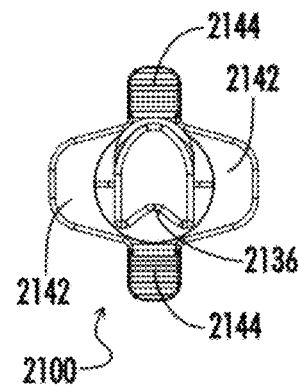
FIG. 21D illustrates a bottom view of the device of FIG. 21A.
Figure 22A:
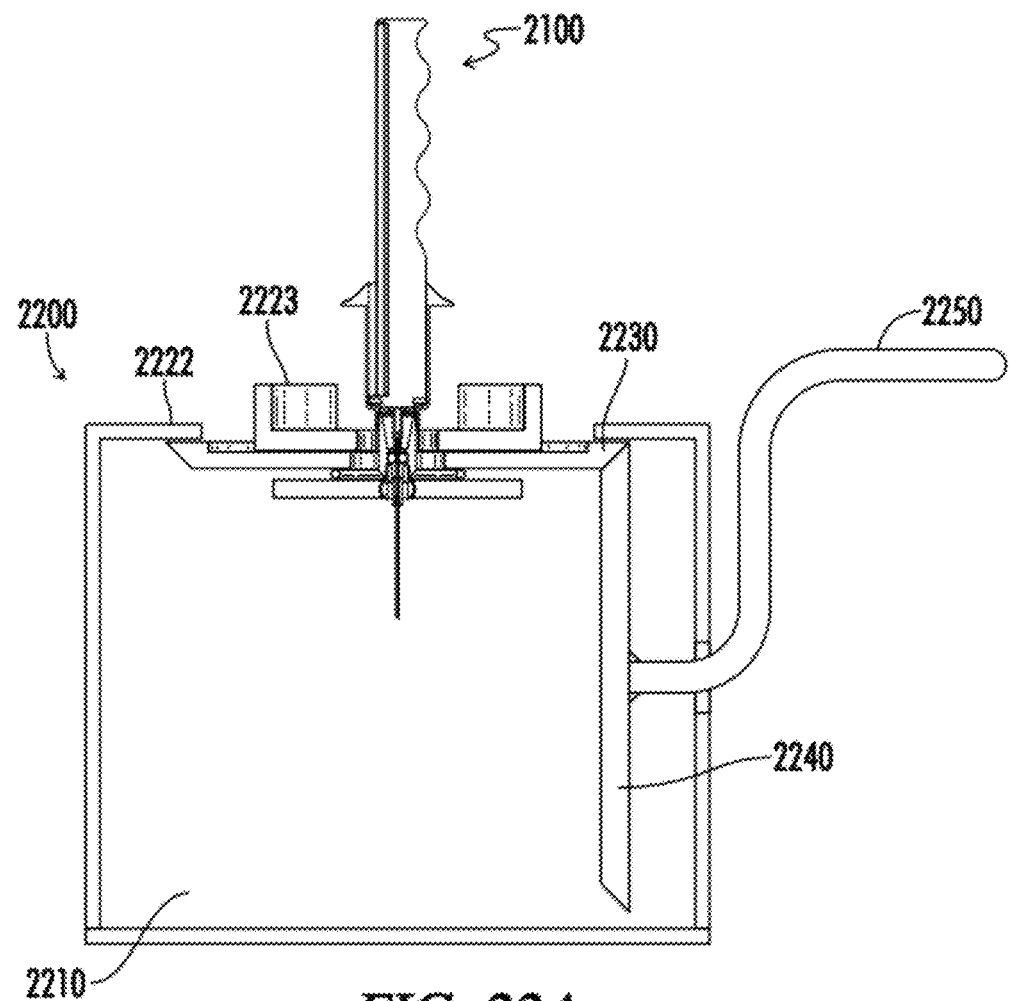
FIG. 22A illustrates a cross-section of an alternative embodiment of a collection container.
Figure 22B:
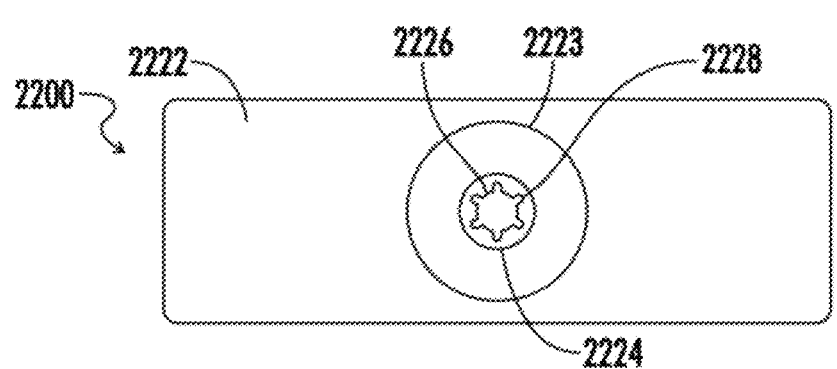
FIG. 22B illustrates one embodiment of a top view of a component of the container of FIG. 22A.
Figure 22C:
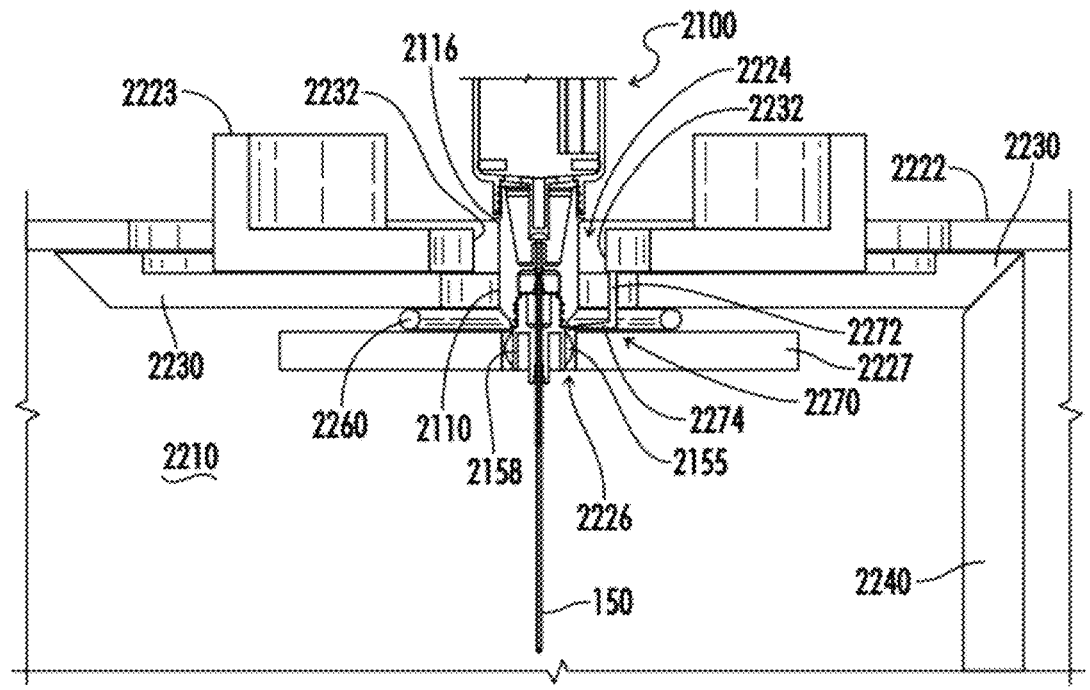
FIG. 22C illustrates a partial cross-section of one embodiment of the container of FIG. 22A.
Figure 22D:
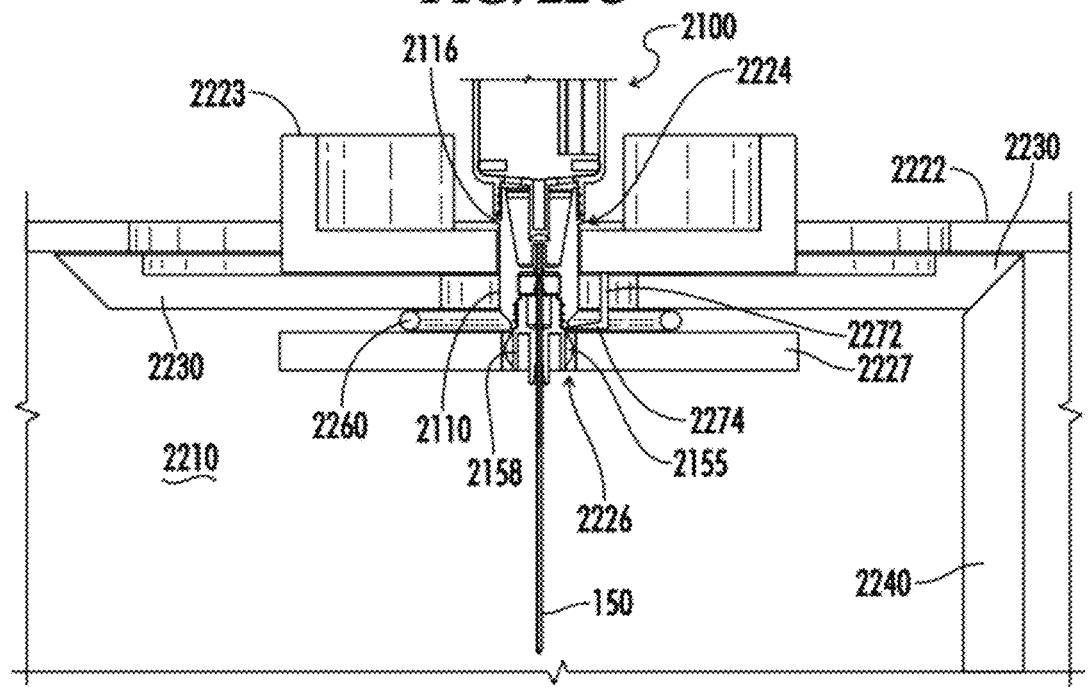
FIG. 22D illustrates a partial cross-section of one embodiment of the container of FIG. 22A.

In one embodiment, insertion of the device 1800 into the first component 1920 automatically activates the gears 1930 as described above. In another embodiment, the gears 1930 may be activated by an external switch (not shown) that must be manually activated by a user. In another embodiment, a detecting system such as a light beam source (ultra-red light or laser beam, for example) (not shown) and a sensor may be used to activate a switch, wherein insertion of the device 1800 into the first component 1920 interrupts a light beam detected on a sensor that triggers the switch to activate the gears. In another embodiment shown in FIG. 20 that does not rely on gears or the like, there is provided a container 2000 having a first opening 2010 for the passage of the device hub 1810 and a second opening 2020 provided with slots 2025 to capture only the wings 1855 of the needle holder 1858 (FIG. 18) to anchor the needle holder 1858 relative to the hub 1810, such that the hub 1858 and device 1800 may be manually rotated while the needle holder 1858 remains captured within the second opening 2020 until the needle holder 1858 separates from the hub 1810 and drops into the interior 2030 of the container 2000. The interior 2030 may be removable from the container 2000 or the entire container 2000 may be disposable. Other configurations are possible.

Figure 19H:
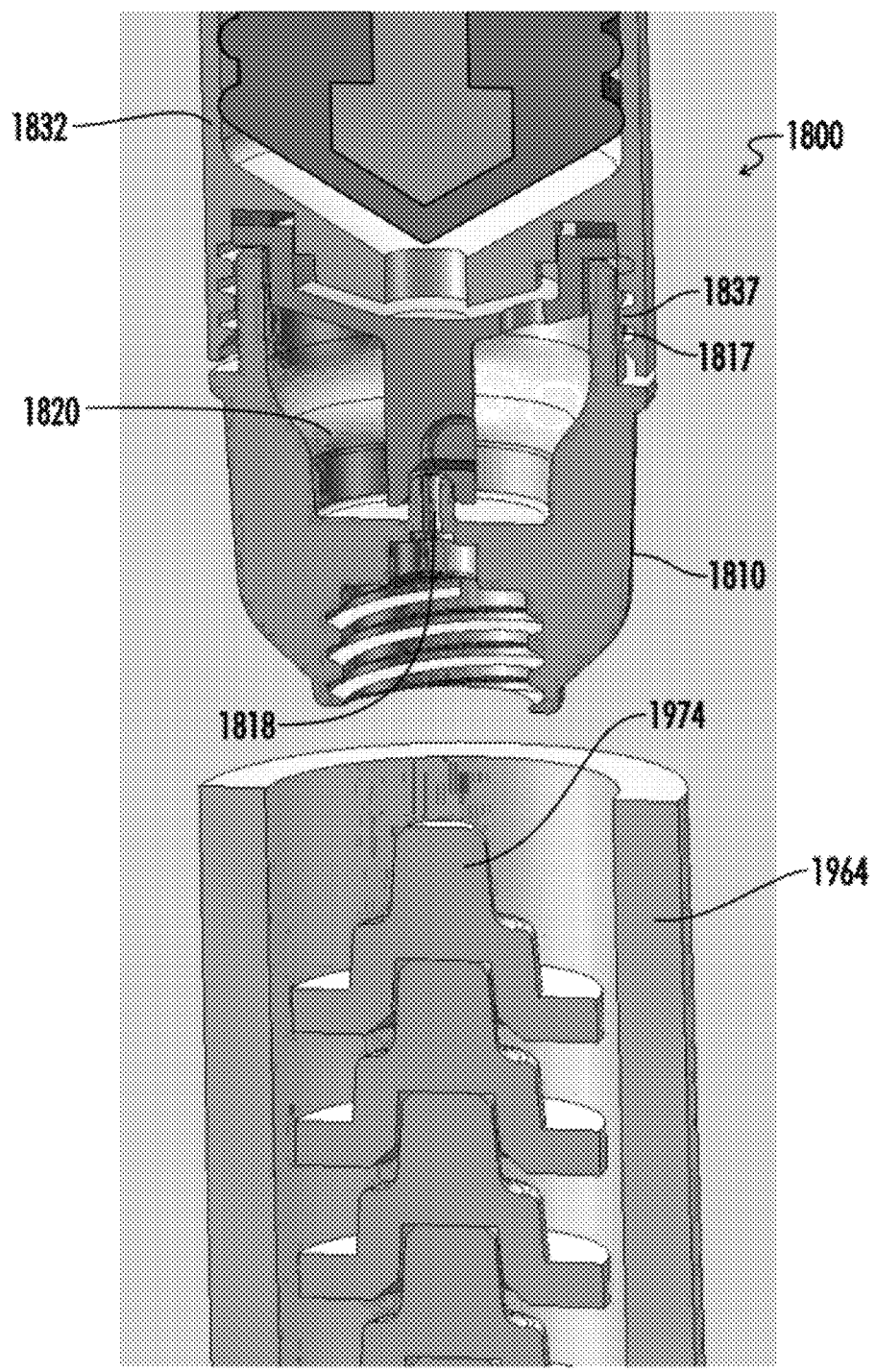
Figure 19I:
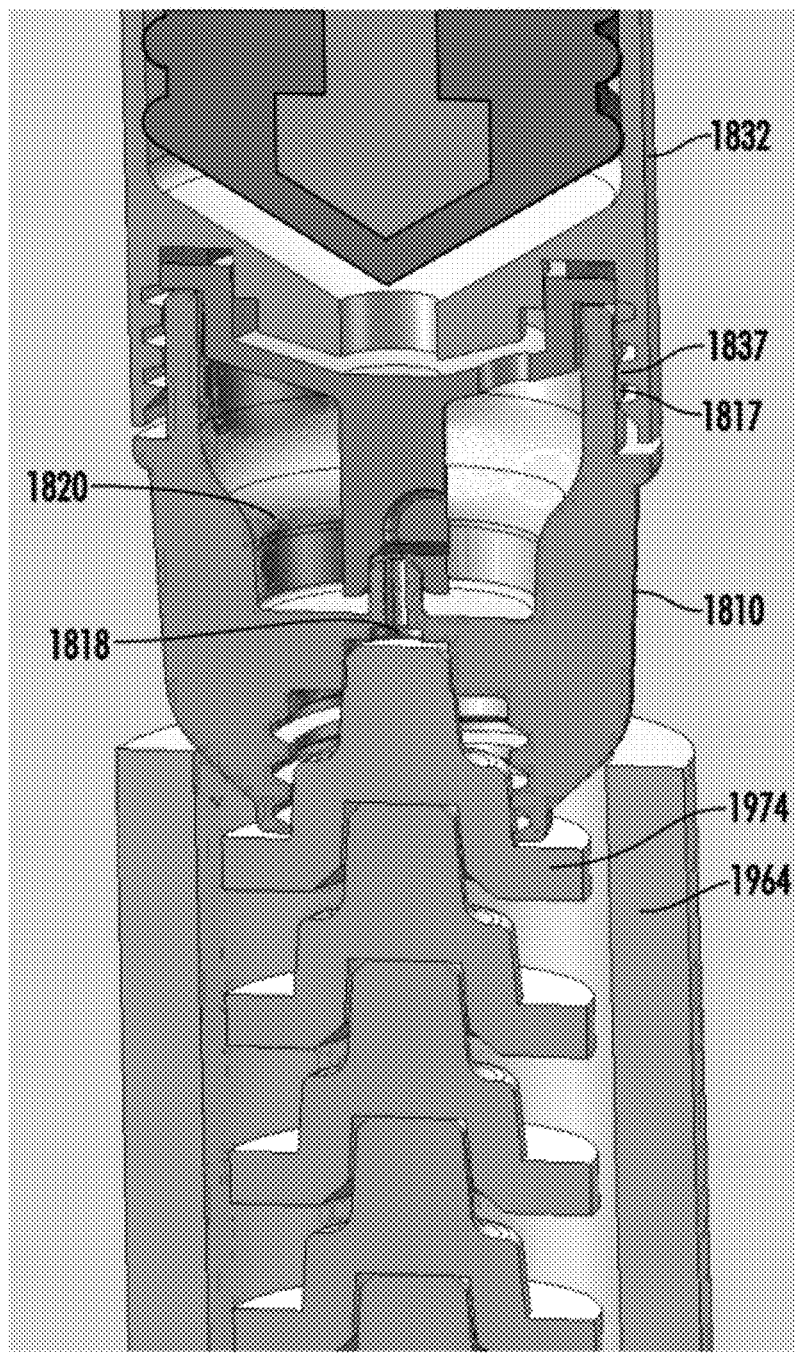
FIG. 19I illustrates an engagement of the portion of a biopsy device with the component of an embodiment of the container shown in FIG. 19G.

Returning now to FIG. 19G, the third component 1960 is utilized after the needle holder 1858 (FIG. 18) and needle 150 have been removed from the device hub 1810 and it is desired to plug the device hub 1810 in preparation for transport and analysis of a specimen collected within. The third component 1960 further comprises a cover 1962 having an opening 1963 and a tube 1964 extending through the opening 1963 and having a collar 1966 that prevents the tube 1964 from passing completely through the opening 1963. The tube 1964 slides along a support core 1968 that extends upwardly from a floor 1970, the tube 1964 being attached to the floor 1970 by a spring 1972 that extends around the support core 1968. The tube 1964 is biased away from the floor 1970 such that the collar 1966 contacts the cover 1962 when the spring 1972 is fully biased away from the floor 1970. A plurality of plugs 1974 is stacked within the tube 1964 in preparation for engagement with the device hub 1810 as shown in FIG. 19H. In the embodiment of FIG. 19I, the device hub 1810 is pressed against the tube 1964 and forces the tube 1964 downward along the support core 1968 until the device hub 1810 engages with and attaches to a plug 1974 to seal the channel 1818 and the hub chamber 1820 of the device hub 1810. Thereafter, the hub 1810 and plug 1974 are removed from the tube 1964. The engagement of the hub 1810 with the plug 1974 may be a press-fit engagement or a threaded engagement (not shown). Other methods of engagement are possible. After all of the plugs 1974 have been depleted and the tube 1964 is fully extended relative to the floor 1970, an additional series of plugs 1974 may be introduced into the tube 1964 in preparation for engagement with a device 1800 as described herein.

The plug 1974 may comprise a sealing material including, but not limited to a silicone, polymers, rubber or the like. If, for example, the needle 150 is truncated (not shown) instead of being completely removed from the hub 1810, such as if the needle is not attached to a needle holder or the like, the truncated portion of the needle would penetrate into the seal material in the plug 1974 and seal any possible opening of the needle and the hub 1810.

Thus, the container 1900 may serve two distinct functions. The first component 1920 may be used to separate a removable needle 150 from a device hub 1810, wherein the removable needle 150 is properly and safely disposed within the second component 1940. This might occur after the device 1800 is used to collect a specimen within the hub 1810. Alternatively, the first component 1920 may be used to truncate a needle 150 (not shown) so that only a minor portion of the needle 150 remains. Thereafter, the hub 1810 with specimen may be plugged with a plug 1974 from the third component 1960 so that the device 1800 is now ready to be transported for analysis of the specimen.

FIGS. 21A-21D illustrate an alternative embodiment of a multifunction aspiration biopsy device 2100 having a removable hub 2110, an internal hub chamber 2120 for the collection of a specimen (not shown), a vacuum source 2130 defined by a barrel 2132 and a plunger 2134, and a needle 150 held by a needle holder 2158 that is removably attached via an external thread 2159, for example, to a hub extension 2180 extending from the hub 2110. The sidewall 2114 of the hub 2110 further comprises a circumferential rim 2116 and terminates in an external thread 2117 that threadingly engages an internal thread 2137 (FIG. 21C) on the barrel 2132 so that the hub 2110 is removable from the barrel 2132 as previously described in many embodiments herein. The sidewall 2114 of the hub 2110 is further provided with at least one and more preferably a plurality of extensions or wings 2115 for improved gripping and for engagement with a collection container as will be described below. The needle holder 2158 is also provided with at least one and more preferably a plurality of extensions or wings 2155 for improved gripping and for engagement with a collection container as described in the various embodiments below. In the illustrated embodiment of FIGS. 21A-21D, the hub extensions 2115 extend outwardly a greater diameter than the needle holder extensions 2155, however the hub extensions 2115 may also extend outwardly at the same or at a lesser diameter than the needle holder extensions 2155. While the embodiment of FIGS. 21A-21D illustrates a certain number of extensions 2115, 2155, it will be appreciated that any number, size, diameter or other configuration may be possible.

The vacuum source 2130 in the embodiment of FIGS. 21A-21D is further provided with a barrel rim 2140 having a plurality of laterally extending finger tabs 2142 and a plurality of downwardly extending finger tabs 2144. While a spaced-apart combination of a pair of laterally extending finger tabs 2142 and a pair of downwardly extending finger tabs 2144 are shown, it will be appreciated that the barrel rim 2140 may be populated with only laterally extending finger tabs 2142, or only downwardly extending finger tabs 2144, or other numbers of tabs, or a different combination of the same other than what is shown in the figures. Furthermore, while the tabs 2142, 2144 are arranged at ninety degree intervals, it will be appreciated that other spacing is possible. For certain users, the downwardly extending finger tabs 2144 may be easier and more comfortable to handle than the laterally extending finger tabs 2142. The plunger 2134 further comprises a contoured body having a plurality of spaced-apart finger grasps 2135 and a longitudinally-extending elongated groove 2136, each for gripping by a different part of the user's hand (not shown).

FIGS. 22A-23C illustrate partial cross-sectional views of various embodiments of a collection container 2200, 2300 that is adapted to receive a multifunction aspiration biopsy device 2100 having an attached needle 150. While multifunction aspiration biopsy device 2100 of FIGS. 21A-21D is used herein for purposes of explaining the construction and use of the collection container 2200, it will be appreciated that the container 2200 may be used with other biopsy devices or needles as desired. Other constructional variations are possible. In one embodiment shown in FIGS. 22A-22D, the collection container 2200 supports the needle holder 2158 in place and then engages the device hub 2110 to rotate the device hub 2110 relative to the needle holder 2158 to thereby separate the needle holder 2158 from the device hub 2110. In another embodiment shown in FIGS. 23A-23C, the collection container 2300 supports the device hub 2110 in place and then engages the needle holder 2158 to rotate the needle holder 2158 relative to the device hub 2110 to thereby separate the needle holder 2158 from the device hub 2110.

More specifically, in the embodiment of FIGS. 22A-22D, the collection container 2200 further comprises an interior 2210 for receiving used or detached needles 150, and an outer surface 2222 having a first opening 2224 that is at least partially surrounded, and more preferably completed surrounded by a wall 2223 extending upwardly from the outer surface 2222. The first opening 2224 is dimensioned to receive the device hub 2110 and allow for the passage of the needle holder 2158 into a second opening 2226 provided on a support arm 2227 within the interior 2210 of the container 2200. The second opening 2226 has slots 2228 (shown more clearly in the top view of the container 2200 of FIG. 22B) that engage and capture the wings 2155 on the needle holder 2158. The second opening 2226 is fixed within the support arm 2227 in the interior 2210 of the container 2200 and functions to support and anchor the needle holder 2158 relative to the device hub 2110.

The container 2200 further comprises at least one and preferably a pair of gears 2230 having teeth 2232 that engage the wings 2115 on the device hub 2110. The gears 2230 are driven by a driving gear 2240 that, in the illustrated embodiment, is driven by a manually-operated handle 2250. While a handle 2250 is illustrated, it will be appreciated that other driving devices may be used, such as an electrical motor or some other power system now known or hereinafter developed. A spacer such as a spacer ring 2260 is provided between the gears 2230 and the support arm 2227 to loosely connect the gears 2230 and the support arm 2227 while allowing the gears 2230 to rotate relative to the support arm 2227. The gears 2230 are movable, upon activation of the driving gear 2240 by the handle 2250 or the like, between a first position shown in FIG. 22C that is spaced from the device hub 2110 to allow for insertion of the needle holder 2158 into the interior 2210 of the container 2200, and a second position shown in FIG. 22D that is engaged with the device hub 2210 and more particularly the wings 2115 of the device hub 2110. Upon engagement of the gear teeth 2232 with the wings 2115 of the device hub 2110, rotation of the gears 2230 causes a rotation of the device hub 2110, and the remainder of the device 2100 above the device hub 2110, relative to the needle holder 2158 that has been captured in the second opening 2226 until the needle holder 2158 with needle 150 separates from the device hub 2110 and drops into the interior 2210 of the container 2200.

The separation of the needle holder 2158 from the device hub 2110 is facilitated by the use of an extraction member 2270 having an extraction arm 2272 that is attached to the gears 2230 and an extraction finger 2274 that is initially situated between the device hub 2110 and needle holder 2158 and that is initially biased downward against the needle holder 2158. Upon rotation of the device hub 2110 relative to the needle holder 2158 that results in the exposure of the external thread 2159 of the needle holder, the extraction finger 2274 engages with and rides along the external thread 2159 on the needle holder 2158. Upon the final rotation of the device hub 2110 relative to the needle holder 2158 and the point of separation between the device hub 2110 and needle holder 2158, the bias provided by the extraction finger 2274 against the needle holder 2158 forces the needle holder 2158 away from the device hub 2110 and into the interior 2210 of the container 2200. While the use of an extraction member 2270 is shown, it will be appreciated that such extraction member 2270 is optional, and the needle holder 2158 may simply fall into the interior 2210 of the container 2200 through gravity alone.

Figure 23A:
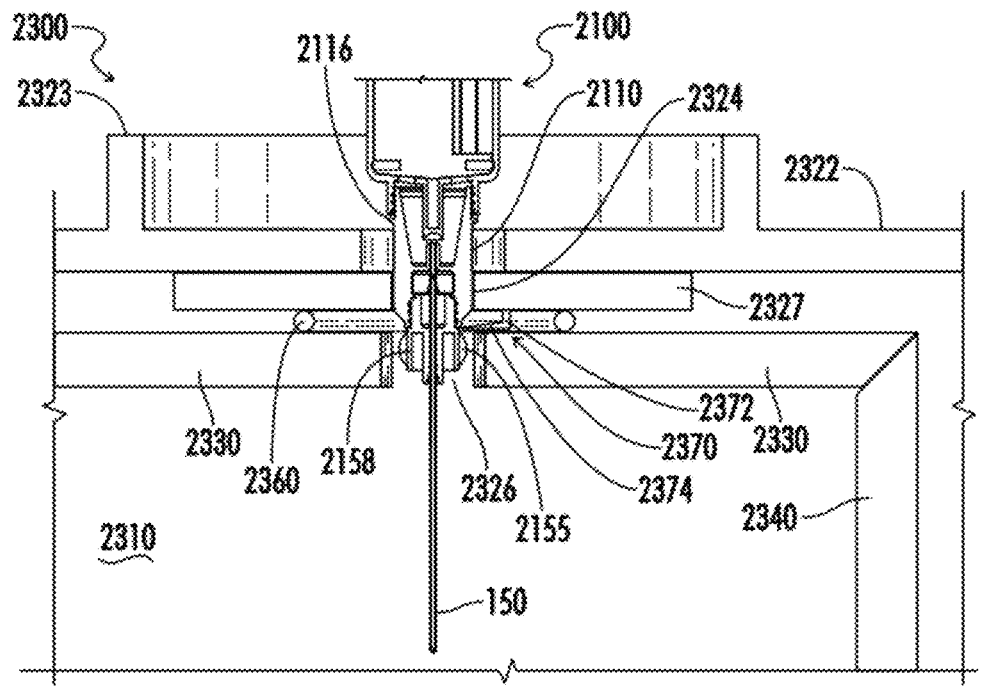
FIG. 23A illustrates a cross-section of an alternative embodiment of a collection container.
Figure 23B:
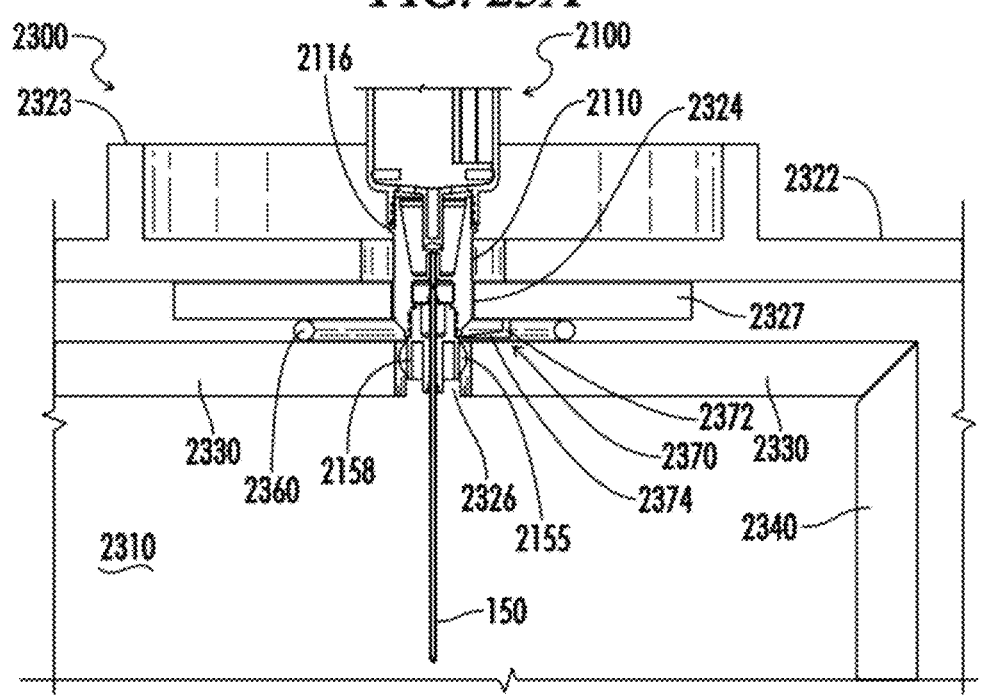
FIG. 23B illustrates a partial cross-section of one embodiment of the container of FIG. 23A.

Alternatively, in the embodiment of FIGS. 23A-23C, the collection container 2300 further comprises an interior 2310 for receiving used or detached needles 150, and an outer surface 2322 having a first opening 2324 provided on a support arm 2327 that is at least partially surrounded, and more preferably completed surrounded by a wall 2323 extending upwardly from the outer surface 2322. The first opening 2324 is dimensioned to receive the device hub 2110 and allow for the passage of the needle holder 2158 into a second opening 2326 within the interior 2310 of the container 2300. The first opening 2324 is fixed within the support arm 2327 and has slots 2328 (shown more clearly in a diagrammatic version of the top view of the container 2300 of FIG. 23C) that engage and capture the wings 2115 on the device hub 2110 and functions to support and anchor the device hub 2110 relative to the needle holder 2158.

The container 2300 further comprises at least one and preferably a pair of gears 2330 having teeth 2332 that engage the wings 2155 on the needle holder 2158. The gears 2330 are driven by a driving gear 2340 that, in the illustrated embodiment, is driven by a manually-operated handle (not shown), such as the handle 2250 of the embodiment of FIGS. 22A-22D, for example. While a handle is described, it will be appreciated that other driving devices may be used, such as an electrical motor or some other power system now known or hereinafter developed. A spacer such as a spacer ring 2360 is provided between the gears 2330 and the support arm 2327 to loosely connect the gears 2330 and the support arm 2327 while allowing the gears 2330 to rotate relative to the support arm 2327. The gears 2330 are movable, upon activation of the driving gear 2340 by a handle or the like, between a first position shown in FIG. 23A that is spaced from the needle holder 2158 to allow for insertion of the needle holder 2158 into the interior 2310 of the container 2300, and a second position shown in FIG. 23B that is engaged with the needle holder 2158 and more particularly the wings 2155 of the needle holder 2158. Upon engagement of the gear teeth 2332 with the wings 2155 of the needle holder 2158, rotation of the gears 2330 causes a rotation of the needle holder 2158 relative to the device hub 2110 that has been captured in the first opening 2324 until the needle holder 2158 with needle 150 separates from the device hub 2110 and drops into the interior 2310 of the container 2300.

The separation of the needle holder 2158 from the device hub 2110 is facilitated by the use of an extraction member 2370 having an extraction arm 2372 that is attached to the support arm 2327 and an extraction finger 2374 that is initially situated between the device hub 2110 and needle holder 2158 and that is initially biased downward against the needle holder 2158. Upon rotation of the needle holder 2158 relative to the device hub 2110 that results in the exposure of the external thread 2159 of the needle holder, the extraction finger 2274 engages with and rides along the external thread 2159 on the needle holder 2158. Upon the final rotation of the needle holder 2158 relative to the device hub 2110 and the point of separation between the device hub 2110 and needle holder 2158, the bias provided by the extraction finger 2374 against the needle holder 2158 forces the needle holder 2158 away from the device hub 2110 and into the interior 2310 of the container 2300. While the use of an extraction member 2370 is shown, it will be appreciated that such extraction member 2370 is optional, and the needle holder 2158 may simply fall into the interior 2310 of the container 2300 through gravity alone.

The multifunction device of the various embodiments of present disclosure can have a variety of uses. Once a specimen has been collected in the hub chamber, and once the hub chamber has been detached from the vacuum source and from the needle, the collected specimen can be triaged in a variety of manners. For example, the collected specimen can be divided into different portions for different biomedical tests. In addition, the hub chamber and collected specimen can be sealed, as set forth in FIGS. 7A through 9, for example, and used as a centrifugation tube. Thus, the user of the multifunction device can collect a specimen and triage the specimen without needing to transfer the collected specimen to another centrifugation tube, for example. Thus, the sealed hub chamber and collected specimen can be used as a specimen transfer tube to deliver the collected specimen to a desired location. In addition, the sealed chamber with collected specimen can be used for cell or microorganism culture, or as a test tube for different tests of the collected specimen. In addition, the chamber with collected specimen can be used to prepare a cell block, where a mixing matrix is added to the collected specimen to form a cell block that is then removed from the hub chamber and analyzed or transferred to a cassette for analysis. Other uses are contemplated.

For example, various embodiments of the previously described multifunction aspiration and biopsy device could also be used in combination with other devices to function as both a collection system and an injection system, wherein a portion of the device can be used to collect a specimen from a target area and can also be used to deliver material to the same target area using a different device, and vice versa. For example, referring back to the hub embodiment 1510*b* of FIGS. 15C-15D, there is provided a needle 150 that is used to obtain a specimen that collects on the hub floor 1516*b*. Once the specimen collection is complete from the target area, the needle 150 is removed from the hub 1510*b* at which point the hub chamber 1520*b* is re-sealed relative to the channel 1518*b* through the use of seal 1505*b* and a cover (not shown in FIG. 15C) may be applied to the hub 1510*b* for transport and analysis of the specimen. The needle 150, though the use of a carrier such as the detached needle holder 1558*b*, may then be attached to another device such as an injection device 2400 of FIG. 24, to deliver an injection material 2444 through the same needle 150 to the target area (not shown).

The injection device 2400 of the embodiment of FIG. 24 is comprised of a vacuum device 2430 including a barrel 2432 and a plunger 2434 movable within the barrel 2432. The barrel 2432 further comprises a sidewall 2436 having a barrel extension 2437 and a barrel floor 2438 that limits movement of the plunger 2434 relative to the barrel 2432, the barrel floor 2438 and barrel sidewall 2436 defining a barrel chamber 2440 that may include an injection material 2444. The barrel floor 2438 further comprises an opening or channel 2418 for extension of the outlet 154 of the needle 150 therethrough, and a seal 2405 that extends across the channel 2418 and is preferably attached to the undersurface 2417 of the barrel floor 2438 within the barrel extension 2437 by any means now known or hereinafter developed, such as by adhesives or the like. The seal 2405 initially seals the barrel chamber 2440 from the opening created by the channel 2418 and prevents the injection material 2444 from escaping from the barrel chamber 2440. When it is desired to attach the needle 150 to the injection device 2400 in order to deliver the injection material 2444 through the needle 150 and to the target area, the outer thread 1559*b* of the needle holder 1558*b* is threadingly engaged with the inner thread 2439 on the barrel extension 2437 until the needle outlet 154 penetrates through the seal 2405 and through the channel 2418 in order to create fluid communication between the barrel chamber 2440 and the needle 150. Thereafter, the needle 150 is used to deliver the injection material 2444 from the barrel chamber 2440 to the target area (not shown).

In an alternative embodiment, the needle holder 1558*b* and needle 150 may first be connected to the injection device 2400 for injecting the injection material 2444 to a target area (not shown). Thereafter, the needle 150 and needle holder 1558*b* may be detached from the barrel extension 2437 and attached to a collection device such as any of the collection devices described herein, such as the hub 1510*b* of FIG. 15C for example, for the collection of cells and other material from the same or different target area (not shown).

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

While the foregoing description and drawings represent the exemplary embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, sizes, and with other elements, materials, and components, without departing from the spirit or essential characteristics thereof. One skilled in the art will appreciate that the invention may be used with many modifications of structure, arrangement, proportions, sizes, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being defined by the appended claims, and not limited to the foregoing description or embodiments.

What is claimed is:

1. An apparatus comprising:
   a) a hub having a hub chamber for receiving a collected specimen, the hub chamber comprising a hub floor, and for receiving the collected specimen through a channel in the hub floor,
   b) a vacuum source in communication with the hub chamber,
   c) a needle detachable from the hub and having an outlet in communication with the hub chamber, and
   d) a cover within the hub chamber extending over a portion of the needle outlet for directing a specimen collected through the needle into the hub chamber in a direction that differs from a longitudinal axis of the hub chamber,
   e) wherein the needle has proximate and distal ends and a straight segment at the proximate end, the proximate end being in direct communication with the hub chamber through the channel, wherein the needle further comprises a lumen for engaging with a stylet.

2. The apparatus of claim 1, wherein the cover is attached to the vacuum source.

3. The apparatus of claim 1, wherein the cover is formed as part of the channel.

4. The apparatus of claim 1, wherein the cover is formed as part of the hub floor.

5. The apparatus of claim 1, wherein the cover is formed as part of a sidewall of the hub.

6. The apparatus of claim 1, wherein the needle further comprises a stylet having a core that occupies the lumen of the needle and that is removable from the needle lumen through the hub chamber, the stylet further comprising an anchor for manipulating the core relative to the needle lumen.

7. The apparatus of claim 1, further comprising a removable container disposed within the hub chamber for receiving a collected specimen.

8. The apparatus of claim 1, further comprising a first seal in the cover.

9. The apparatus of claim 1, wherein the hub is separable from the vacuum source and the needle, and wherein the hub chamber of a separated hub is sealable with a cap that seals one end of the hub and a plug that seals an opposite end of the hub.

10. The apparatus of claim 9, wherein the plug further comprises a sealing member that seals a channel in the hub floor through which the needle extends when the needle is attached to the hub.

11. The apparatus of claim 10, wherein the sealing member further comprises a core that extends into the channel and an anchor for manipulating the core.

12. The apparatus of claim 10, wherein an inner surface of the cap further comprises a moisture matrix to retain moisture of a collected specimen in the hub chamber.

13. The apparatus of claim 9, wherein the cap is vented.

* * * * *